United States Patent

Pierce et al.

[11] Patent Number: 6,040,480
[45] Date of Patent: Mar. 21, 2000

[54] ASYMMETRIC SYNTHESIS OF BENZOXAZINONES

[75] Inventors: Michael E. Pierce, Wilmington, Del.; Cheng Y. Chen, Colonia, N.J.; Anusuya Choudhury, Landenberg, Pa.; Lilian A. Radesca, Newark, Del.; Lushi Tan, Edison; Dalian Zhao, Fanwood, both of N.J.

[73] Assignee: Du Pont Pharmaceuticals Company, Wilmington, Del.

[21] Appl. No.: 09/248,567

[22] Filed: Feb. 11, 1999

Related U.S. Application Data

[62] Division of application No. 09/055,480, Apr. 6, 1998, Pat. No. 5,925,789
[60] Provisional application No. 60/042,803, Apr. 7, 1997.

[51] Int. Cl.[7] .................................................. C07C 215/00
[52] U.S. Cl. .......................... 564/390; 564/413; 564/442; 564/443
[58] Field of Search .................................. 564/390, 413, 564/442, 443

[56] References Cited

U.S. PATENT DOCUMENTS 3,967,835  7/1976  Ozutsumi et al. ...................... 282/27.5
5,519,021  5/1996  Young et al. .

FOREIGN PATENT DOCUMENTS 831092   11/1975  Belgium .
582455A  2/1994   European Pat. Off. .
9520389  8/1995   WIPO .
9622955  8/1996   WIPO .
9637457  11/1996  WIPO .

OTHER PUBLICATIONS

Young et al., Antimicrobial Agents & Chemotherapy, 1995, 39, No. 12, pp. 2602–2605.

Thompson et al., Tetrahedron Letters, 1995, 36, No. 49, pp. 8937–8940.

Takai, H. et al. Chem. Pharm. Bull., 1985, 33, (3), pp. 1129–1139, "Spiropiperidines. I. Synthesis of 1'–Substituted Spiro[4H–3, 1–benzoxazine–4,4'–piperidin]–2(1H)–one Derivatives and Evaluation of Their Antihypertensive Activity".

*Primary Examiner*—Samuel Barts

[57] ABSTRACT

The present invention provides novel methods for the asymmetric synthesis of (S)-6-chloro-4-cyclopropylethynyl-4-trifluoromethyl-1,4-dihydro-2H-3,1-benzoxazin-2-one of formula (VI-i)

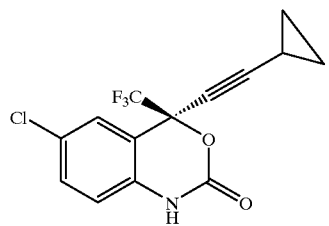

(VI-i)

which is useful as a human immunodeficiency virus (HIV) reverse transcriptase inhibitor.

3 Claims, No Drawings

ASYMMETRIC SYNTHESIS OF BENZOXAZINONES

This is a divisional of Ser. No. 09/055,480 filed Apr. 6, 1998, now U.S. Pat. No. 5,925,789; which claims the benefit of U.S. Provisional Application No. 60/042,803, filed Apr. 7, 1997.

FIELD OF THE INVENTION

The present invention provides novel methods for the asymmetric synthesis of (S)-6-chloro-4-cyclopropylethynyl-4-trifluoromethyl-1,4-dihydro-2H-3,1-benzoxazin-2-one which is useful as human immunodeficiency virus (HIV) reverse transcriptase inhibitor.

BACKGROUND OF THE INVENTION

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication.

A number of compounds are effective in the treatment the human immunodeficiency virus (HIV) which is the retrovirus that causes progressive destruction of the human immune system with the resultant onset of AIDS. Effective treatment through inhibition of HIV reverse transcriptase is known for both nucleoside based inhibitors, such as azidothymidine, and non-nucleoside based inhibitors. Benzoxazinones have been found to be useful non-nucleoside based inhibitors of HIV reverse transcriptase. The (S)-6-chloro-4-cyclopropylethynyl-4-trifluoromethyl-1,4-dihydro-2H-3,1-benzoxazin-2-one of formula (VI-i):

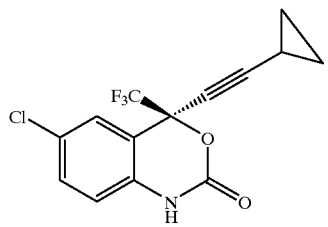

is not only a highly potent reverse transcriptase inhibitor, it is also efficacious against HIV reverse transcriptase resistance. Due to the importance of (S)-6-chloro-4-cyclopropylethynyl-4-trifluoromethyl-1,4-dihydro-2H-3,1-benzoxazin-2-one as a reverse transcriptase inhibitor, economical and efficient synthetic processes for its production need to be developed.

Thompson et al, *Tetrahedron Letters* 1995, 36, 937–940, describe the asymmetric synthesis of an enantiomeric benzoxazinone by a highly enantioselective acetylide addition followed by cyclization with a condensing agent to form the benzoxazinone shown below.

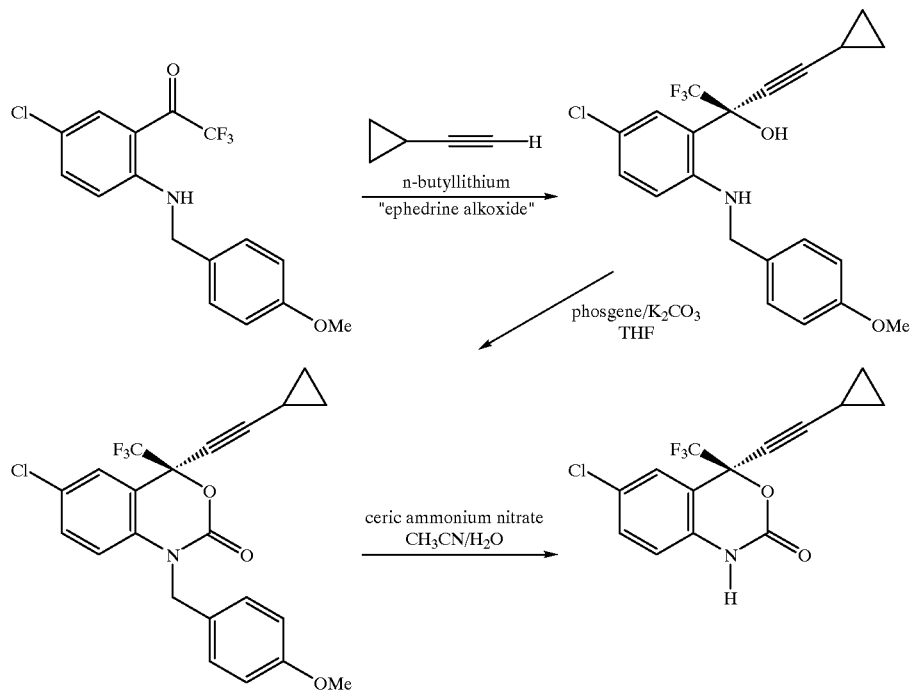

The p-methoxybenzyl aniline starting material is synthesized by benzylating the aniline nitrogen with p-methoxybenzyl chloride. Additionally, the overall process generates a large volume of heavy metal waste in the waste stream due to ceric ammonium nitrate oxidation in the debenzylation step.

European Patent Application 582,455 A1 describes the synthesis of benzoxazinones via a three step process.

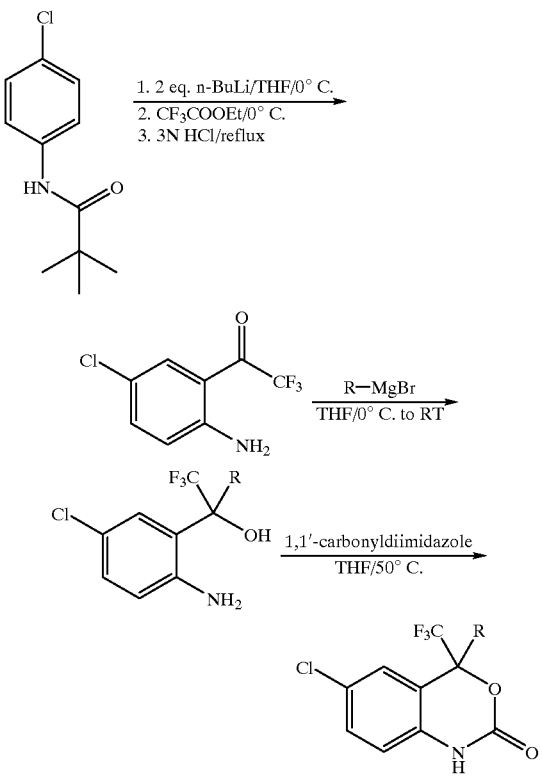

This general method teaches (1) metallation of the pivalamide of parachloroaniline with n-butyllithium followed by nucleophilic substitution with an ester to form a ketone, (2) synthesis of a tertiary carbinol by Grignard addition to the ketone, and (3) cyclization of the unprotected amine with the carbinol by addition of a large excess of condensing agent to form a benzoxazinone. The process requires further purification of the optical isomers through use of an optically active resolving agent such as (−)camphanic acid.

Young et al, PCT International Patent Application Number WO 9520389 A1 describe benzoxazinones useful in the inhibition of HIV reverse transcriptase, the prevention or treatment of infection by HIV and the treatment of AIDS. Application WO 9520389 A1 discloses methods of synthesis which are commensurate with EP 582,455 A1 above. Additionally, Young et al, *Antimicrobial Agents and Chemotherapy* 1995, 39, 2602–2605, in discussing the clinical benefit, the in vitro activity, and the pharmacokinetic activity of benzoxazinone (VI) in the treatment of HIV as an HIV reverse transcriptase inhibitor disclose an abbreviated synthesis of benzoxazinone (VI) commensurate with EP 582,455 A1 above wherein the tertiary carbinol is synthesized by addition of a cyclopropylethynyl-lithium reagent before cyclizing the unprotected amine with the carbinol by addition of a condensing agent.

Thompson et al, PCT International Patent Application Number WO 9622955 A1 describe an improved synthesis of cyclopropylacetylene useful in the synthesis of (S)-6-chloro-4-cyclopropylethynyl-4-trifluoromethyl-1,4-dihydro-2H-3,1-benzoxazin-2-one. Application WO 9622955 A1 discloses combinations of synthetic methods disclosed in the publications above which continue to be inefficient in the overall synthesis for which this invention makes significant improvements.

The above methods for the syntheses of benzoxazinones use combinations of toxic, difficult to handle reagents, relatively expensive materials and inefficient chromatographic purification steps or generally overall synthesis of (S)-6-chloro-4-cyclopropylethynyl-4-trifluoromethyl-1,4-dihydro-2H-3,1-benzoxazin-2-one in low yields. Thus, it is desirable to discover new synthetic routes to benzoxazinones on a large scale which improve upon these limitations and provide high yields of desired benzoxazinones.

Accordingly, the present invention provides for a novel benzylating procedure, using acid catalyzed benzyl alcohols instead of the corresponding benzyl chloride analogues, which can be more expensive and unstable. Optimization of the procedure allows for streamlined processing since the product does not require isolation.

The present invention provides the preparation of (1R, 2S)-pyrrolidinyl norephedrine as such pure product that it may be used as a solution stream reagent in the chiral addition of lithium cyclopropylacetylide. The present invention provides the preparation of cyclopropylacetylene as such pure product that it too may be used as a solution stream reagent in the chiral addition of the cyclopropylacetylide anion, for example, lithium cyclopropylacetylide.

The present invention provides an improved synthetic process for the asymmetric synthesis of benzoxazinones. The process of the present invention eliminates the use of highly toxic ceric ammonium nitrate, thus eliminating cerium ions in the waste stream. The present invention provides for an efficient non-chromatographic purification process to yield enantiomericly pure product. Additionally, the present invention provides for intermediates as stable solids purifiable by recrystallization.

None of the above-cited references describe the methods of the present invention for the synthesis of benzoxazinones useful as inhibitors of HIV reverse transcriptase.

SUMMARY OF THE INVENTION

The present invention concerns novel processes for the preparation of benzoxazinone compounds which are useful as HIV reverse transcriptase inhibitors. The processes provide for a novel benzylating procedure of primary amines, using acid catalyzed benzyl alcohols. The processes of the present invention provide high yields, can be conducted on a kilogram scale, and yield stable intermediates. The invention further provides for a nonchromatographic separation to improve overall yield.

There is provided by this invention a process for the preparation of a compound of formula (VI):

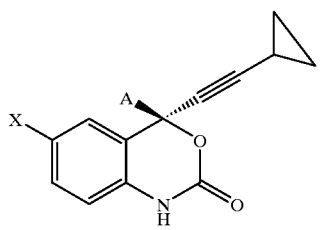

wherein:

X is Cl or F, and

A is —CF₃, —C₂F₅ or —C₃F₇;

said process comprising one or more of the following:

(1) (addition) contacting a compound of formula (I):

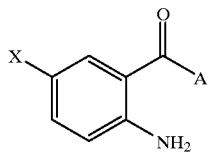
(I)

with a compound of formula (VII) or formula (VIII):

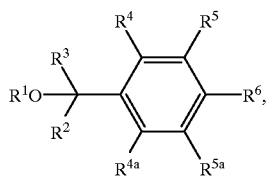
(VII)

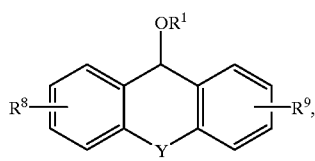
(VIII)

wherein:
$R^1$ is H or $C_{1-6}$ alkyl,
$R^2$ is H, —$CH_3$, —$CH_2CH_3$ or phenyl substituted with 0–3 $R^{12}$,
$R^3$ is H, —$CH_3$, —$CH_2CH_3$ or phenyl substituted with 0–3 $R^{12}$,
$R^4, R^5, R^{4a}, R^{5a}, R^6, R^8$ and $R^9$ are independently selected from H, $C_{1-6}$ alkyl, $C_{1-6}$ alkoxy and $C_{1-6}$ alkylthio,
$R^{12}$ is H, $C_{1-6}$ alkyl, $C_{1-6}$ alkoxy or $C_{1-6}$ alkylthio;
Y is —$(CH_2)_n$ or O, and
n is 0, 1, 2 or 3;
in the presence of methane sulfonic acid, p-toluene sulfonic acid or another suitable acid catalyst to form a compound of formula (II):

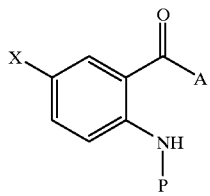
(II)

wherein
P is

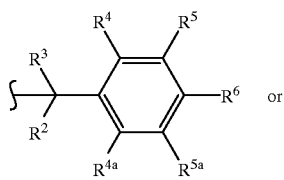

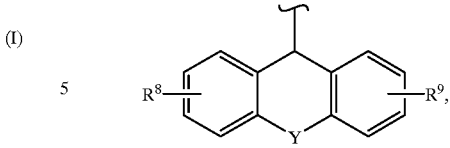

(2) (chiral addition) (a) contacting 1R,2S-pyrrolidinyl norephedrine with n-hexyl lithium or another suitable alkyl lithium and cyclopropylacetylene to form a mixture, (b) contacting the mixture of Step(2)(a) with a compound of formula (II) to form a compound of formula (III):

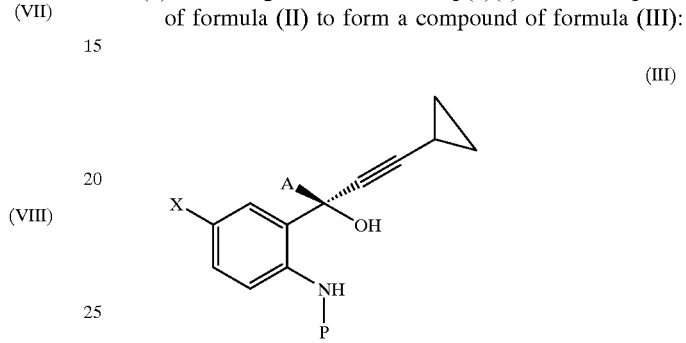
(III)

(3) (oxidative cyclization) contacting a compound of formula (III) with p-chloranil or another suitable oxidizing agent to form a compound of formula (IV):

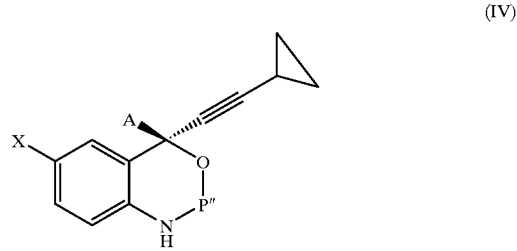
(IV)

wherein
P″ is

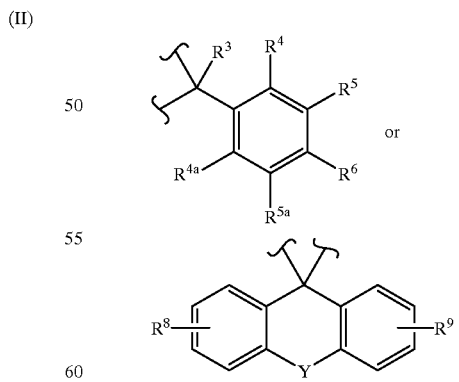

(4) (debenzylation) contacting the compound of formula (IV) with potassium hydroxide, sodium hydroxide or another suitable cleaving agent, in the presence of sodium borohydride or another suitable trapping agent, to form a compound of formula (V):

(V)

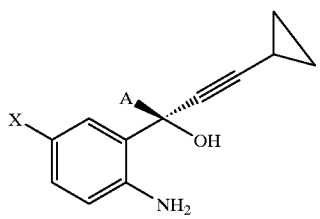

(5) (cyclization) contacting the compound of formula (V) with phosgene or another suitable cyclizing agent to form a compound of formula (VI).

DETAILED DESCRIPTION OF THE INVENTION

In a first embodiment, the present invention provides a novel process for the preparation of compounds of formula (VI):

(VI)

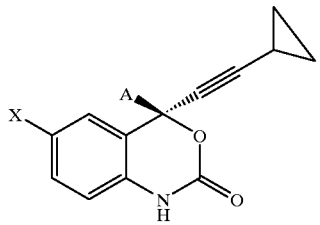

wherein:

X is Cl or F, and
A is —$CF_3$, —$C_2F_5$ or —$C_3F_7$;

said process comprising:

(1) contacting a compound of formula (I):

(I)

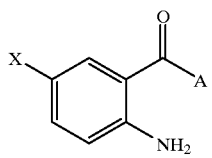

with a compound of formula (VII) or formula (VIII):

(VII)

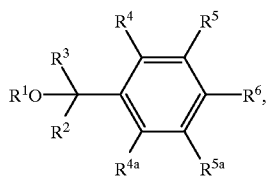

-continued (VIII)

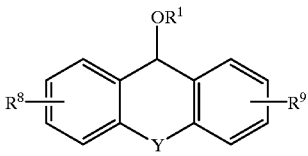

wherein:
$R^1$ is H, $C_{1-6}$ alkyl or $C_{1-6}$ alkylcarbonyl,
$R^2$ is H,
$R^3$ is H, —$CH_3$, —$CH_2CH_3$ or phenyl substituted with 0–3 $R^{12}$,
$R^4, R^5, R^{4a}, R^{5a}, R^6, R^8$ and $R^9$ are independently selected from H, $C_{1-6}$ alkyl, $C_{1-6}$ alkoxy and $C_{1-6}$ alkylthio,
$R^{12}$ is H, $C_{1-6}$ alkyl, $C_{1-6}$ alkoxy or $C_{1-6}$ alkylthio;
Y is —$(CH_2)_n$— or O, and
n is 0, 1, 2 or 3;
in a suitable solvent, in the presence of a suitable acid catalyst to form a compound of formula (II):

(II)

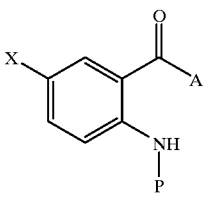

wherein
P, an amine protecting group, is

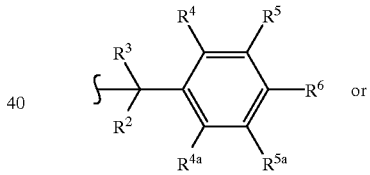

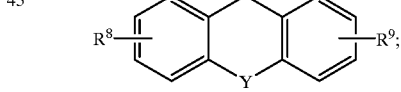

(2)(a) contacting a compound of formula (IX):

(IX)

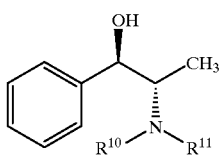

wherein
$R^{10}$ and $R^{11}$ are independently $C_{1-4}$ alkyl, or
—$NR^{10}R^{11}$ is pyrrolidinyl, piperidinyl or morpholinyl;
with alkyl lithium and cyclopropylacetylene, in a suitable solvent, to form a mixture, and
(b) contacting the mixture of step (2)(a) with a compound formula (II) to form a compound of formula (III):

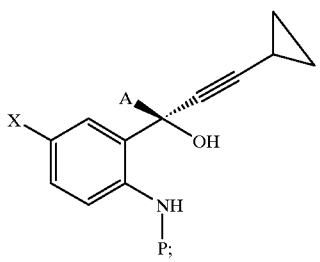

(III)

(3) contacting a compound of formula (III), in a suitable nonaqueous solvent, with a suitable oxidizing agent to form a compound of formula (IV):

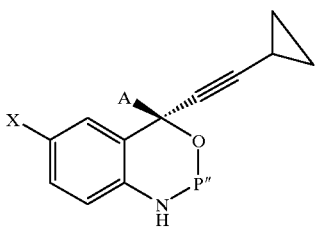

(IV)

wherein
P″ is

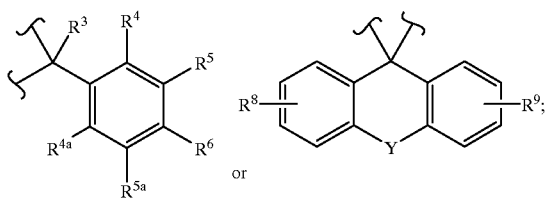

or (4) contacting a compound of formula (IV) with a suitable cleaving agent, in a suitable solvent, in the presence of a suitable trapping agent, to form a compound of formula (V):

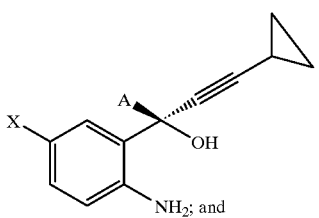

(V)

(5) contacting a compound of formula (V) with a suitable cyclizing agent, in a suitable solvent, to form a compound of formula (VI).

In a preferred embodiment the process for the preparation of a compound of formula (VI), wherein
X is Cl, and
A is —CF$_3$;
comprises:

(1) contacting a compound of formula (I) with a compound of formula (VII), wherein:
R$^1$ is H, C$_{1-6}$ alkyl or C$_{1-6}$ alkylcarbonyl,
R$^2$ is H,
R$^3$ is H, —CH$_3$, —CH$_2$CH$_3$ or phenyl substituted with 0–3 R$^{12}$,
R$^4$, R$^5$, R$^{4a}$, R$^{5a}$ and R$^6$ are independently selected from H, C$_{1-6}$ alkyl, C$_{1-6}$ alkoxy and C$_{1-6}$ alkylthio, and
R$^{12}$ is H, C$_{1-6}$ alkyl, C$_{1-6}$ alkoxy or C$_{1-6}$ alkylthio;

in a suitable solvent, in the presence of a suitable acid catalyst to form a compound of formula (II);

(2)(a) contacting 1R,2S-pyrrolidinyl norephedrine with n-hexyl lithium and cyclopropylacetylene, in a suitable solvent, to form a mixture, and (b) contacting the mixture of step (2)(a) with a compound of formula (II) to form a compound of formula (III);

(3) contacting a compound of formula (III) with a suitable oxidizing agent, in a suitable solvent, to form a compound of formula (IV);

(4) contacting a compound of formula (IV) with a suitable cleaving agent, in a suitable solvent, in the presence of a suitable trapping agent, to form a compound of formula (V); and (5) contacting a compound of formula (V) with a suitable cyclizing agent, in a suitable solvent, to form a compound of formula (VI).

In a more preferred embodiment the process for the preparation of a compound of formula (VI-i):

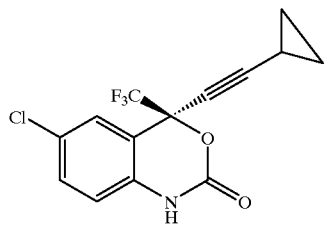

(VI-i)

comprises:

(1) contacting a compound of formula (I), wherein X is Cl and A is trifluoromethyl, with p-methoxybenzyl alcohol, in a suitable solvent, in the presence of a suitable acid catalyst, to form a compound of formula (II-i):

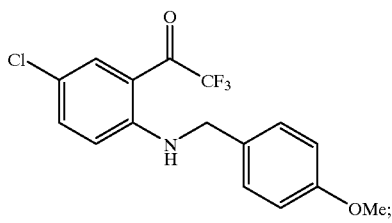

(II-i)

(2)(a) contacting 1R,2S-pyrrolidinyl norephedrine with n-hexyl lithium and cyclopropylacetylene, in a suitable solvent, to form a mixture, (b) contacting the mixture of step (2)(a) with a compound of formula (II-i) to form a compound of formula (III-i):

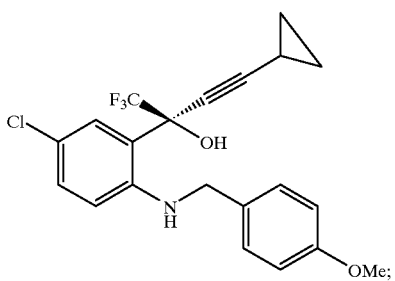

(III-i)

(3) contacting a compound of formula (III-i) with a suitable oxidizing agent, in a suitable solvent, to form a compound of formula (IV-i):

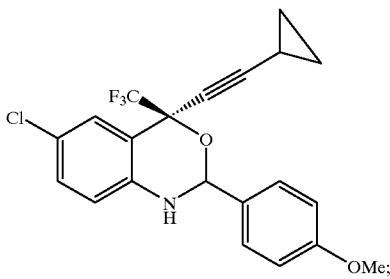

(IV-i)

(4) contacting a compound of formula (IV-i) with a suitable cleaving agent, in a suitable solvent, in the presence of a suitable trapping agent, to form a compound of formula (V-i):

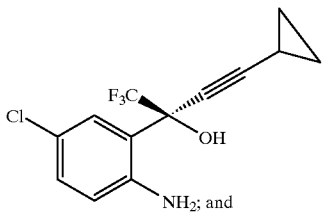

(V-i)

(5) contacting a compound of formula (V-i) with a suitable cyclizing agent, in a suitable solvent, to form a compound of formula (VI-i).

In an even more preferred embodiment in a process for the preparation of a compound of formula (VI):
the suitable acid catalyst is selected from the group:
  HCl, methanesulfonic acid, benzenesulfonic acid, phosphoric acid, sulfuric acid, trifluoroacetic acid, trichloroacetic acid and p-toluene-sulfonic acid,
the suitable oxidizing agent is selected from the group:
  $MnO_2$, 2,3-dichloro-5,6-dicyano-1,4-benzoquinone, p-tetrachlorobenzoquinone, o-tetrachlorobenzoquinone and iodosobenzene diacetate,
the suitable cleaving agent is selected from the group:
  sodium $C_{1-4}$ alkoxide, lithium $C_{1-4}$ alkoxide, potassium $C_{1-4}$ alkoxide, NaOH, LiOH, KOH and $Ca(OH)_2$,
the suitable trapping agent is $NaBH_4$, $NaHSO_3$, hydroxyl amine, tosyl hydrazide or $H_2O_2$, and
the suitable cyclizing agent is phosgene.

In an even further more preferred embodiment in a process for the preparation of a compound of formula (VI) the compounds of step (2)(a) and (b) are independently prepared and mixed as solution streams.

In a second embodiment, the present invention provides a process for the preparation of compounds of formula (II):

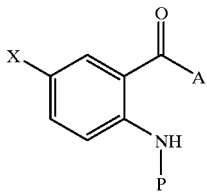

(II)

wherein:

X is Cl or F,

A is $-CF_3$, $-C_2F_5$ or $-C_3F_7$,

P is

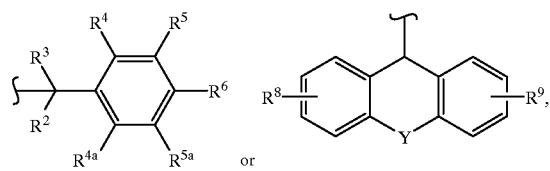

$R^2$ is H, $-CH_3$, $-CH_2CH_3$ or phenyl substituted with 0–3 $R^{12}$, $R^3$ is H, $-CH_3$, $-CH_2CH_3$ or phenyl substituted with 0–3 $R^{12}$, $R^4$, $R^5$, $R^{4a}$, $R^{5a}$, $R^6$, $R^8$ and $R^9$ are independently selected from H, $C_{1-6}$ alkyl, $C_{1-6}$ alkoxy and $C_{1-6}$ alkylthio, $R^{12}$ is H, $C_{1-6}$ alkyl, $C_{1-6}$ alkylthio or $C_{1-6}$ alkoxy;

Y is $-(CH_2)_n$ or O, and n is 0, 1, 2 or 3;

said process comprising:

contacting a compound of formula (I):

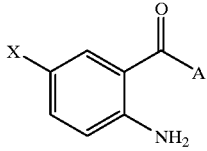

(I)

with a compound of formula (VII) or formula (VIII):

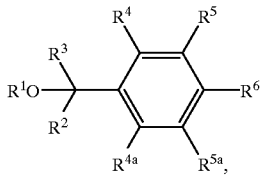

(VII)

-continued (VIII)

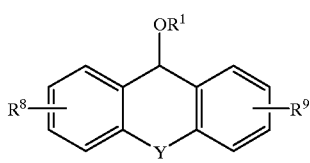

wherein
R¹ is H, $C_{1-6}$ alkyl or $C_{1-6}$ alkylcarbonyl,
in a suitable solvent, in the presence of a suitable acid catalyst to form a compound of formula (II).

In a preferred embodiment a compound of formula (VII) is

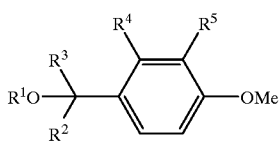

R¹ is H or methyl,
R² is H or phenyl substituted with H or methoxy,
R³ is H or phenyl substituted with H or methoxy,
R⁴ is H or methoxy, and
R⁵ is H or methoxy.

In a further preferred embodiment a suitable acid catalyst is selected from the group: HCl, methanesulfonic acid, benzenesulfonic acid, phosphoric acid, sulfuric acid, trichloroacetic acid, trifluoroacetic acid and p-toluene-sulfonic acid.

In a third embodiment, the present invention provides a process for the preparation of compounds of formula (IV):

(IV)

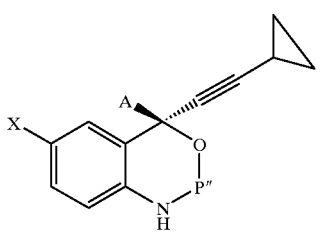

wherein:
X is Cl or F,
A is —CF₃, —C₂F₅ or —C₃F₇,
P″ is

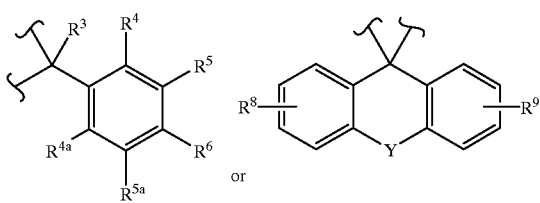

R³ is H, —CH₃, —CH₂CH₃ or phenyl substituted with 0–3 $R^{12}$,
R⁴, R⁵, R⁴ᵃ, R⁵ᵃ, R⁶, R⁸ and R⁹ are independently selected from H, $C_{1-6}$ alkyl, $C_{1-6}$ alkoxy and $C_{1-6}$ alkylthio, R¹² is H, $C_{1-6}$ alkyl, $C_{1-6}$ alkylthio or $C_{1-6}$ alkoxy,
Y is —(CH₂)ₙ or O, and
n is 0, 1, 2 or 3;

said process comprising:

contacting a compound of formula (III):

(III)

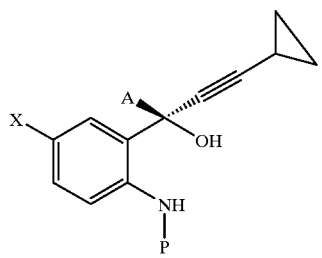

wherein:

P is

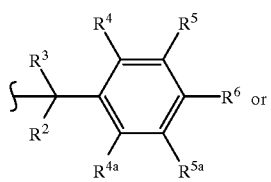

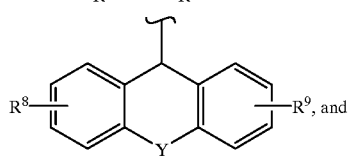

R² is H, in a nonaqueous solvent, with a suitable oxidizing agent to form a compound of formula (IV).

In a preferred embodiment a compound of formula (III) is

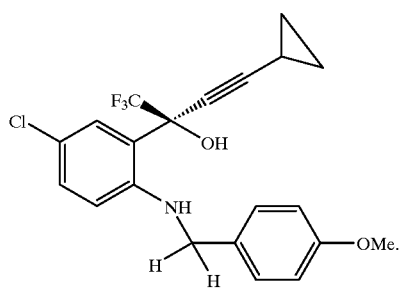

In a more preferred embodiment the suitable oxidizing agent is selected from the group MnO₂, 2,3-dichloro-5,6-dicyano-1,4-benzoquinone, p-tetrachlorobenzoquinone, o-tetrachlorobenzoquinone and iodosobenzene diacetate.

In a fourth embodiment, the present invention provides a process for the preparation of compounds of formula (V):

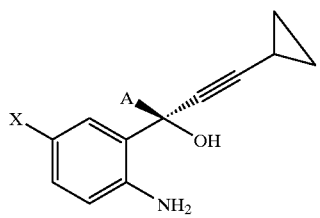

wherein:

X is Cl or F, and

A is —CF$_3$, —C$_2$F$_5$ or —C$_3$F$_7$;

said process comprising:

contacting the compound of formula (IV):

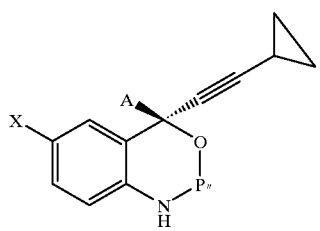

wherein

P" is

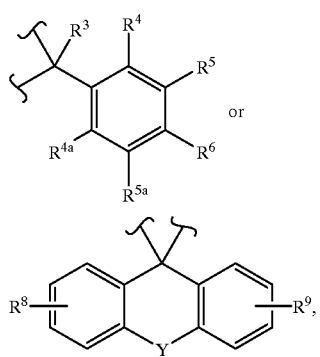

R$^3$ is H, —CH$_3$, —CH$_2$CH$_3$ or phenyl substituted with 0–3 R$^{12}$,

R$^4$, R$^5$, R$^{4a}$, R$^{5a}$, R$^6$, R$^8$ and R$^9$ are independently selected from H, C$_{1-6}$ alkyl, C$_{1-6}$ alkoxy and C$_{1-6}$ alkylthio, R$^{12}$ is H, C$_{1-6}$ alkyl, C$_{1-6}$ alkylthio or C$_{1-6}$ alkoxy;

Y is —(CH$_2$)$_n$ or O, and n is 0, 1, 2 or 3;

with a suitable cleaving agent, in a suitable solvent, in the presence of a suitable trapping agent, to form a compound of formula (V).

In a preferred embodiment a compound of formula (IV) is

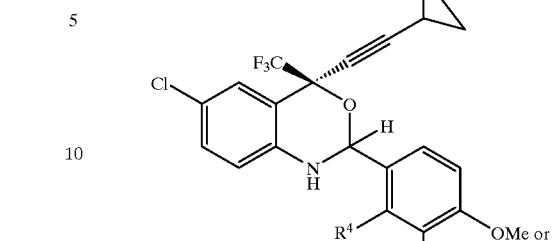

R$^3$ is phenyl substituted with H or methoxy,

R$^4$ is H or methoxy, and

R$^5$ is H or methoxy.

In a more preferred embodiment the suitable cleaving agent is selected from the group: sodium C$_{1-4}$ alkoxide, lithium C$_{1-4}$ alkoxide, potassium C$_{1-4}$ alkoxide, NaOH, LiOH, KOH and Ca(OH)$_2$, and the suitable trapping agent is selected from the group: NaBH$_4$, NaHSO$_3$, hydroxyl amine, tosyl hydrazide and H$_2$O$_2$ In a fifth embodiment, the present invention further provides a process for the preparation of a compound of formula (VI):

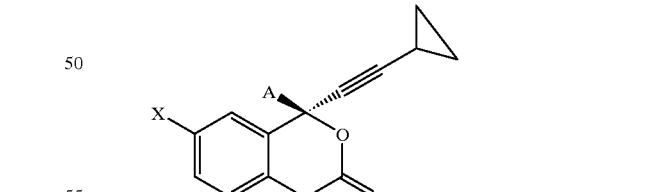

wherein:

X is Cl or F, and

A is —CF$_3$, —C$_2$F$_5$ or —C$_3$F$_7$;

said process comprising:

(1) contacting a compound of formula (I):

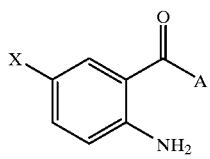
(I)

with a compound of formula (VII):

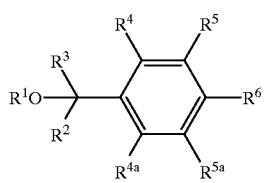
(VII)

wherein:
$R^1$ is H, $C_{1-6}$ alkyl or $C_{1-6}$ alkylcarbonyl,
$R^2$ is —$CH_3$, —$CH_2CH_3$ or phenyl substituted with 0–3 $R^{12}$,
$R^3$ is —$CH_3$, —$CH_2CH_3$ or phenyl substituted with 0–3 $R^{12}$,
$R^4$, $R^5$, $R^{4a}$, $R^{5a}$ and $R^6$ are independently selected from H, $C_{1-6}$ alkyl, $C_{1-6}$ alkoxy and $C_{1-6}$ alkylthio, and
$R^{12}$ is H, $C_{1-6}$ alkyl, $C_{1-6}$ alkoxy or $C_{1-6}$ alkylthio;
in a suitable solvent, in the presence of a suitable acid catalyst to form a compound of formula (II)

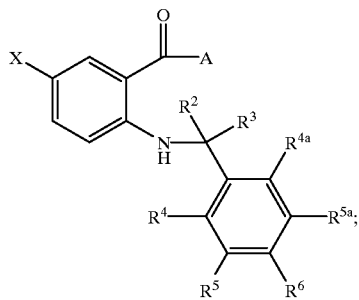
(II)

(2)(a) contacting a compound of formula (IX)

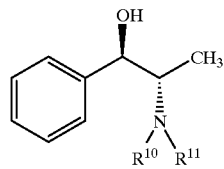
(IX)

wherein
$R^{10}$ and $R^{11}$ are independently $C_{1-4}$ alkyl, or

—$NR^{10}R^{11}$ is pyrrolidinyl, piperidinyl or morpholinyl;
with alkyl lithium and cyclopropylacetylene, in a suitable solvent, to form a mixture, and (b) contacting the mixture of step (2)(a) with a compound formula (II) to form a compound of formula (III):

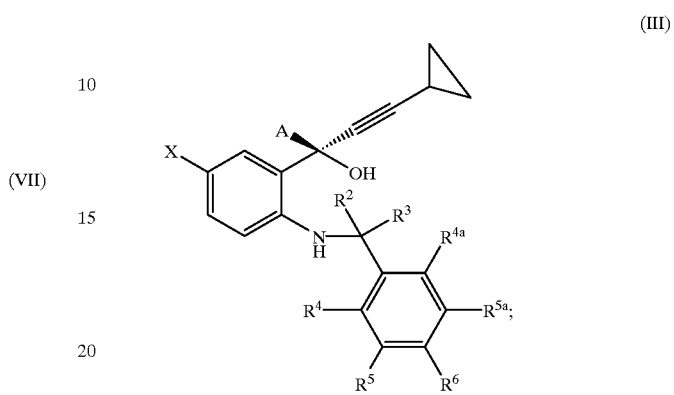
(III)

(3) contacting a compound of formula (III) with a suitable deprotecting agent, in a suitable solvent, to form a compound of formula (V):

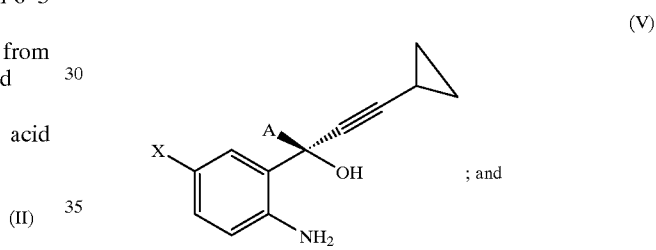
(V)
; and (4) contacting a compound of formula (V) with a suitable cyclizing agent, in a suitable solvent, to form a compound of formula (VI).

In a seventh embodiment, the present invention provides a novel compound of formula (IV-i):

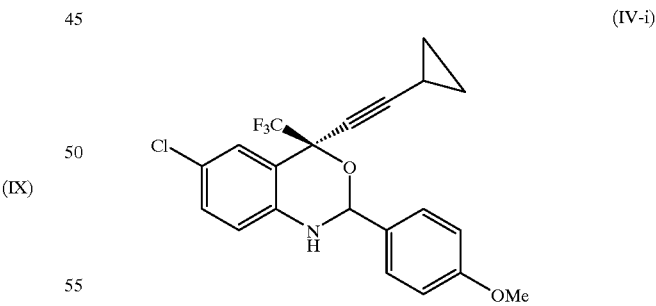
(IV-i)

or a pharmaceutically acceptable salt thereof.

In an eighth embodiment, the present invention provides a process for the preparation of a compound of formula (II-i):

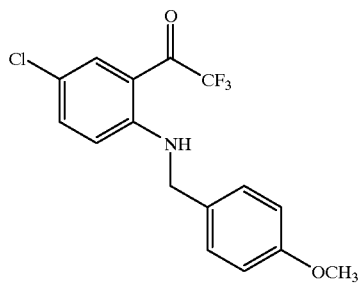

(II-i)

comprising:

(1) heating an acetonitrile solution of a substituted aniline of formula (XII):

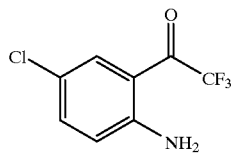

and p-toluenesulfonic acid to a temperature of about 65° C. to about 85° C. while stirring;

(2) adding an acetonitrile solution of a benzyl alcohol of formula (XIII):

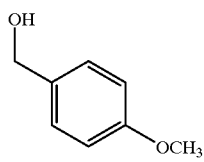

over a period of about 2 hours to about 10 hours to the heated acetonitrile solution of the substituted aniline and p-toluenesulfonic acid; and (3) stirring the heated reaction mixture for about 30 minutes to about 2 hours to give the compound of formula (II-i).

In a preferred embodiment, the process for the preparation of a crystalline compound of formula (II-i):

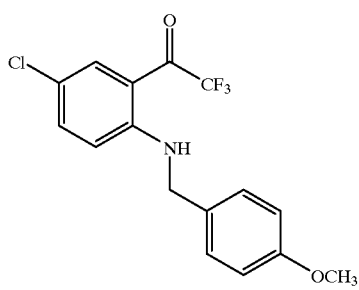

(II-i)

comprises:

(1) heating and stirring an acetonitrile solution of a substituted aniline of formula (XII):

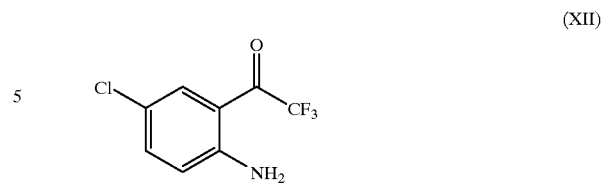

(XII)

and p-toluenesulfonic acid to a temperature of about 65° C. to about 85° C.;

(2) adding an acetonitrile solution of a benzyl alcohol of formula (XIII)

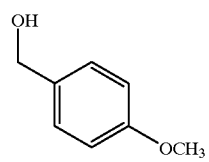

(XIII)

over a period of about 2 hours to about 10 hours to heated acetonitrile solution of the substituted aniline and p-toluenesulfonic acid;

(3) heating and stirring the reaction mixture for about 30 minutes to about 4 hours to give a crude solution of the compound of formula (II-i);

(4) cooling the crude solution of the compound of formula (II-i);

(5) adding seed crystals at a temperature of about 20° C. to about 30° C.;

(6) slowly adding water while stirring at a temperature of about 30° C. to about 35° C. to form a slurry of the crystalline compound of formula (II-i);

(7) stirring the slurry for a reaction time of about 2 hours to about 12 hours at about room temperature;

(8) filtering the slurry of crystalline compound of formula (II-i) to isolate the crystalline compound of formula (II-i);

(9) washing the crystalline material with a mixture of acetonitrile and water in a volume to volume ratio of about 60:40 to about 40:60; and

(10) drying the material under an inert atmosphere at a temperature of about 50° C.

In a ninth embodiment, the present invention provides a process for the preparation of an amino alcohol compound of formula (V-i):

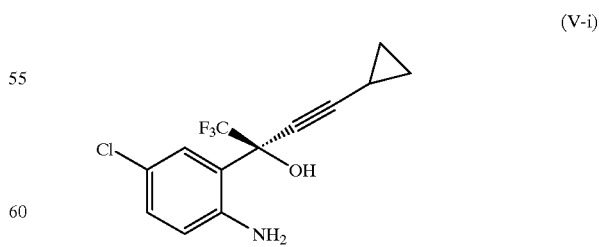

(V-i)

comprising (1) adding a toluene solution of 2,3-dichloro-5,6-dicyano-1,4-benzoquinone to a toluene solution of a compound of formula (III-i):

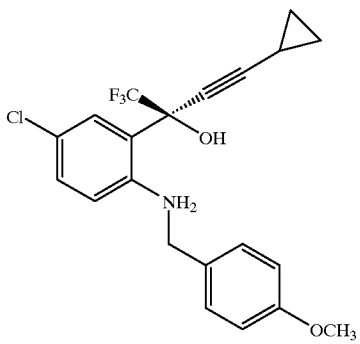

(III-i)

while maintaining a reaction temperature of about 0° C. to about 10° C.;

(2) maintaining the reaction temperature at about 0° C. for about 1 hour to form a toluene slurry of 2,3-dichloro-5,6-dicyano-1,4-dihydroxybenzene and a compound of formula (IV-i):

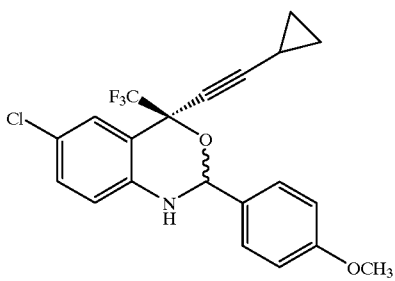

(IV-i)

(3) filtering the slurry to remove the 2,3-dichloro-5,6-dicyano-1,4-dihydroxybenzene;

(4) washing the 2,3-dichloro-5,6-dicyano-1,4-dihydroxybenzene waste cake with toluene;

(5) combining the filtrate and toluene washings;

(6) concentrating in vacuo the filtrate and toluene solution of the compound of formula (IV-i) with methanol to remove most of the toluene;

(7) adding dropwise to the compound of formula (IV-i) in methanol at a temperature of about 40° C. to about 45° C. an aqueous solution of sodium hydroxide forming a clear solution of the amino alcohol and p-methoxy-benzaldehyde;

(8) adding dropwise to the clear solution of the amino alcohol a solution of $NaBH_4$ in an aqueous solution of sodium hydroxide maintaining a reaction temperature of about 40° C. to about 45° C.;

(9) stirring the reaction mixture for about 30 minutes;

(10) neutralizing the reaction with glacial acetic acid to a pH of about 8 to about 9;

(11) adding water to form a slurry;

(12) cooling the slurry to about −15° C. to about 0° C. for about 1 hour; and

(13) filtering the cooled slurry of the amino alcohol and washing with water to give the crude crystalline amino alcohol as a pale yellow solid.

In a preferred embodiment, the present invention provides a process for the preparation of pure crystalline amino alcohol compound of formula (V-i) comprising the additional steps of:

(1) dissolving the crude amino alcohol in toluene at a temperature of about 60° C.;

(2) adding heptane to the toluene solution of the crude amino alcohol to form a slurry of the pure amino alcohol;

(3) cooling the amino alcohol slurry to about 0° C. and maintaining at 0° C. for about 1 hour;

(4) filtering the pure crystalline amino alcohol;

(5) washing the pure crystalline amino alcohol with heptane; and (6) drying the pure crystalline amino alcohol in vacuo In a more preferred embodiment, the present invention provides a process for the preparation of pure crystalline amino alcohol compound of formula (V-i) comprising the additional steps of:

(1) dissolving the crude amino alcohol in a mixture of MTBE-toluene at a temperature of about 20° C. to about 30° C.;

(2) distilling in vacuo the MTBE from the MTBE-toluene solution of the crude amino alcohol;

(3) adding heptane to the toluene solution of the crude amino alcohol to form a slurry of the pure amino alcohol;

(4) cooling the amino alcohol slurry to about 0° C. and maintaining at 0° C. for about 1 hour;

(5) filtering the pure crystalline amino alcohol;

(6) washing the pure crystalline amino alcohol with heptane; and (7) drying the pure crystalline amino alcohol in vacuo.

The processes of the present invention are useful for the preparation of (S)-6-chloro-4-cyclopropylethynyl-4-trifluoromethyl-1,4-dihydro-2H-3,1-benzoxazin-2-one, which is useful as a human immunodeficiency virus (HIV) reverse transcriptase inhibitor and compounds which are useful intermediates in the synthesis of (S)-6-chloro-4-cyclopropylethynyl-4-trifluoromethyl-1,4-dihydro-2H-3,1-benzoxazin-2-one. Such HIV reverse transcriptase inhibitors are useful for the inhibition of HIV and the treatment of HIV infection. Such HIV reverse transcriptase inhibitors are useful for the inhibition of HIV in an ex vivo sample containing HIV or expected to be exposed to HIV. Thus, such HIV reverse transcriptase inhibitors may be used to inhibit HIV present in a body fluid sample (for example, a body fluid or semen sample) which contains or is suspected to contain or be exposed to HIV. Such HIV reverse transcriptase inhibitors are also useful as standards or reference compounds for use in tests or assays for determining the ability of an agent to inhibit viral replication and/or HIV reverse transcriptase, for example in a pharmaceutical research program. Thus, such HIV reverse transcriptase inhibitors may be used as a control or reference compound in such assays and as a quality control standard.

The following terms and abbreviations are used herein and defined as follows. The abbreviation:

"THF" as used herein means tetrahydrofuran,

"DMSO" as used herein means dimethylsulfoxide,

"DMAC" as used herein means dimethylacetamide,

"MTBE" as used herein means methyl t-butyl ether,

"BuLi" as used herein means butyllithium,

"NaH" as used herein means sodium hydride,

"LDA" as used herein means lithium diisopropylamide,

"TsOH" as used herein means p-toluenesulfonic acid,

"TMEDA" as used herein means N,N,N',N',-tetramethylethylenediamine, and

"DDQ" as used herein means 2,3-dichloro-5,6-dicyano-1,4-benzoquinone, and

"DDHQ" as used herein means 2,3-dichloro-5,6-dicyano-1,4-dihydroxybenzene otherwise known as 2,3-dichloro-5,6-dicyano-1,4-dihydrobenzoquinone.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable halogenated solvents include chlorobenzene, fluorobenzene or dichloromethane.

Suitable ether solvents include: tetrahydrofuran, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable basic solvents include: 2-, 3-, or 4-picoline, pyrrole, pyrrolidine, morpholine, pyridine, or piperidine.

Suitable hydrocarbon solvents include: benzene, cyclohexane, pentane, hexane, toluene, cycloheptane, methylcyclohexane, heptane, ethylbenzene, m-, o-, or p-xylene, octane, indane, nonane, or naphthalene.

As used herein, the term "amine protecting group" (or "N-protected") refers to any group known in the art of organic synthesis for the protection of amine groups. Such amine protecting groups include those listed in Greene and Wuts, "Protective Groups in Organic Synthesis" John Wiley & Sons, New York (1991), the disclosure of which is hereby incorporated by reference. Examples of amine protecting groups include, but are not limited to, alkyl types such as benzyl, α-methylbenzyl, diphenylmethyl(benzhydryl), dimethoxybenzhydryl, triphenylmethyl(trityl), 9-fluorenyl, phenylfluorenyl, dihydroanthracenyl, monomethoxytrityl, p-methoxybenzyl, 3,4-dimethoxybenzyl, 2,4-dimethoxybenzyl, 3,4,5-trimethoxybenzyl.

As used herein, the term "chiral inducing agent" or "chiral induction agent" refers to a nonreactive chiral agent which selectively induces the creation of a chiral center in enatiomeric excess upon addition of a nonchiral substrate to a prochiral center. Examples of chiral inducing agents include, but are not limited to, 1R,2S-N-substituted norephedrines such as 1R,2S-N-methylephedrine, 1R,2S-N-pyrrolidinyl norephedrine, 1R,2S-N-piperidinyl norephedrine and 1R,2S-N-morpholinyl norephedrine.

As used herein, the term "acid catalyst" refers to any acidic agent which catalyzes the addition of the alcohol derivative of an alkyl type amine protecting group, such as benzyl alcohol, benzhyrdrol or trityl alcohol, to a free base form of a non-basic amine, such as compound (I). Examples of acid catalysts include, but are not limited to, HCl, HBr, methanesulfonic acid, benzenesulfonic acid, toluenesulfonic acid, sulfuric acid, trifluoroacetic acid, trichloroacetic acid, phosphoric acid and polyphosphoric acid.

As used herein, the term "oxidizing agent" refers to any agent which oxidizes a "benzylic" protected amine to the corresponding imine, thus effecting the formation of compound (IV) from a compound of formula (III) by intramolecular cyclization. Examples of oxidizing agents include, but are not limited to, manganese dioxide, $KMnO_4$, $K_2SO_5$, $KHSO_5$, DDQ, p-chloranil, o-chloranil and iodosobenzene diacetate.

As used herein, the term "deprotecting agent" refers to any acidic agent which can effect the removal of an alkyl type amine protecting group, such as benzyl, benzhydryl or trityl, to a free base form of an amine, such as compound (IV). Examples of deprotecting agents include, but are not limited to, HCl, HBr, methanesulfonic acid, benzenesulfonic acid, trichloroacetic acid, trifluoroacetic acid, phosphoric acid and p-toluenesulfonic acid.

As used herein, the term "cleaving agent" refers to any agent which can effect the formation of a compound of formula (V) by the removal or debenzylation of P" from a hemiaminal of formula (IV). Such cleaving agents are strong bases, examples of which include, but are not limited to, metal hydroxides and metal alkoxides: NaOH, KOH, LiOH, $Ca(OH)_2$, $NaOCH_3$, $NaOC_2H_5$, $NaOC_3H_8$, $NaOC_4H_{10}$, $KOCH_3$, $KOC_2H_5$ and $KOC_4H_{10}$.

As used herein, the term "trapping agent" refers to any agent which can effect the conversion of a byproduct to a material which will not react with the desired product compound (V), wherein, depending on the structure of P", the byproduct is an aromatic aldehyde or ketone upon removal or debenzylation of P" in a hemiaminal of formula (IV). Trapping agents, as used by one skilled in the art, are standard reducing agents, derivatizing agents or oxidizing agents; all of which are used for the selective reaction of one species in a solution over a second species in a solution. Examples of a trapping agent which reduce an aromatic aldehyde or ketone to an alcohol include, but are not limited to, sodium borohydride, lithium borohydride, potassium borohydride, sodium bisulfite and sodium trimethoxyborohydride; wherein sodium borohydride is preferred. Examples of trapping agents which derivatize an aromatic aldehyde or ketone to an oxime or a hydrazone include, but are not limited to, hydrazine, dimethyl hydrazine, hydroxyl amine and tosyl hydrazide. Examples of a trapping agent which oxidize an aromatic aldehyde to an aromatic carboxylic acid include, but are not limited to, hydrogen peroxide, t-butylhydroperoxide, $K_2SO_5$, and $KHSO_5$.

As used herein, the term "cyclizing agent" refers to any agent which can effect the formation of a benzoxazinone from the amino carbinol compound of formula (V). Examples of a cyclizing agent include, but are not limited to, phosgene, 1,1-carbonyldiimidazole, methyl chloroformate and dimethyl carbonate.

As used herein, the term "lithiating agent" or "alkyl lithium" refers to an organolithium reagent which can quantitatively convert an alkyne into a lithium alkynyl. Examples of lithiating agents are, but without limitation, n-hexyllithium, n-octyllithium, n-butyllithium, t-butyllithium, sec-butyllithium, isobutyllithium, lithium diisopropylamide, phenyllithium and triphenylmethyllithium.

"Halo" or "halogen" as used herein refers to fluoro, chloro and bromo.

"Alkyl" as used herein is intended to include both branched and straight chain saturated aliphatic hydrocarbon groups having one to twelve carbon atoms. "Alkoxy" as used herein is intended to include an alkyl group of indicated number of carbon atoms attached through an oxygen bridge; "alkylthio" as used herein is intended to include an alkyl group of indicated number of carbon atoms attached through an sulpher bridge.

The compounds herein described may have asymmetric centers. All chiral, diastereomeric, and racemic forms are included in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

Combinations of substituents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that one or more hydrogen on the designated atom is replaced with a selection from the indicated group, provided that the designated atom's normal valency is not exceeded, and that the substitution results in a stable compound.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The methods of the present invention, by way of example and without limitation, may be further understood by reference to Scheme 1. Scheme 1 details the general synthetic method for asymmetric synthesis of compounds of formulae (I) through (VI) wherein X is Cl and A is trifluoromethyl.

It is to be understood that one skilled in the art of organic synthesis could follow the methods described or exemplified herein to prepare homologues of compounds of formula (I) through (VI) wherein X is Cl or F and A is trifluoromethyl, pentafluoroethyl or heptafluoropropyl, by appropriately choosing a combination of p-chloroaniline or p-fluoroaniline with $CF_3CO_2Et$, $CF_3CF_2CO_2Et$ or $CF_3CF_2CF_2CO_2Et$ in the preparation of compounds of formula (I).

Scheme 1

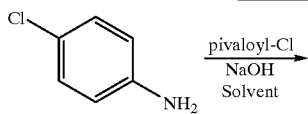

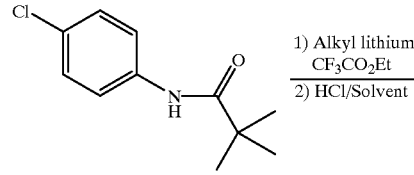

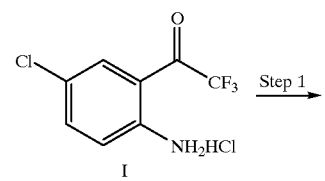

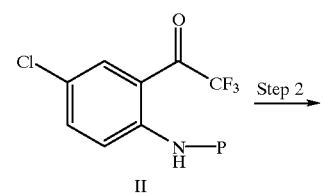

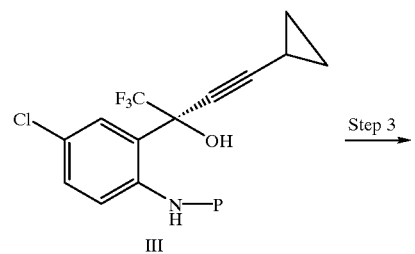

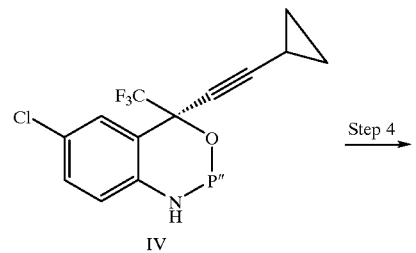

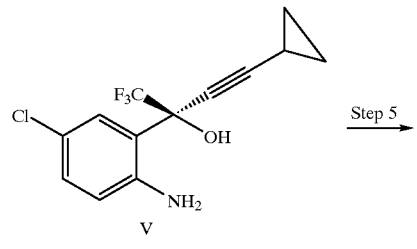

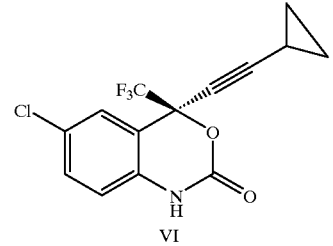

It is the object of the present invention to provide an improved process for the asymmetric synthesis of benzoxazinones which are useful as HIV reverse transcriptase inhibitors.

Step 1: Addition: Preparation of Compound of Formula (II)

This step is conducted by reacting a compound of formula (I), after converting to the free base, in a suitable solvent at a suitable temperature with a benzylic alcohol, a benzylic ether, a benzhydryl alcohol or a benzhydryl ether in the presence of a suitable acid catalyst to form a compound of formula (II). By way of general guidance, compound (I) in an aqueous/organic solvent at about room temperature may be neutralized with base to about pH 7, contacted with about 1 molar equivalent of a benzylic alcohol, a benzylic ether, a benzhydryl alcohol or a benzhydryl ether, additionally contacted with about 0.1 to about 5.0 mole % of a suitable acid catalyst and heated to a temperature sufficient to form compound (II). Compound (II) may be separated from the reaction as a stable solid by standard methods of work up. An example of standard work up is shown in Example 3. Optionally, compound (II) may be carried forward in synthesis of compounds of formula (III).

P is a benzylic or a benzhydryl group derived from a compound of formula (VII) or (VIII), respectively, and is preferably p-methoxybenzyl, 3,4-dimethoxybenzyl, 2,4-dimethoxybenzyl or 4,4'-dimethoxy benzhydryl. More preferably P is p-methoxybenzyl.

Preferred acid catalysts for step (1) include HCl, methane sulfonic acid, sulfuric acid, trifluroacetic acid, trichloroacetic acid and p-toluene-sulfonic acid. More preferred acid catalysts are methane sulfonic acid and p-toluene-sulfonic acid.

Preferred solvents and mixtures thereof for step (1) are toluene, dioxane, ethyl acetate, cyclohexane, dimethoxyethane, methylcyclohexane, 2-propanol and acetic acid. A more preferred solvent is toluene.

A preferred temperature range for step (1) is about room temperature to about 120° C. More preferably when P is p-methoxybenzyl the temperature range is about 60 to about 90° C.

It is understood that one skilled in the art can determine the preferred reaction time of Step 1 as dependent on temperature, acid catalyst and P group. Generally, the reaction time is 0.5 to 12 hours.

Step 2: Chiral Induction: Preparation of Compound of Formula (III)

This step, a chiral induction, comprises the alkylation of an achiral ketone carbonyl of a compound of formula (II) in the presence of a chiral inducing agent of formula (IX) in a suitable solvent with preferably at least about two equivalents of a cyclopropylethynyl lithium, said cyclopropylethynyl lithium being generated in situ for the addition of a cyclopropylethynyl substituent to compound (II) by contacting cyclopropylacetylene with a suitable alkyl lithium, for a suitable length of time at a temperature sufficient to form a compound of formula (III). Generation of about two equivalents of cyclopropylethynyl lithium in situ may be carried out by contacting about two equivalents of cyclopropylacetylene with about four equivalents of a suitable alkyl lithium in a suitable solvent at a temperature below about −0° C. for about 1 to about 3 hours. It is understood by one skilled in the art that about four equivalents of alkyl lithium are required to produce about two quivalents of cyclopropylethynyl lithium because about two equivalents alkyl lithium react with two equivalents of the chiral inducing agent. By way of general guidance about two equivalents of a chiral inducing agent of formula (IX), about four equivalents of a suitable alkyl lithium and about two equivalents of cyclopropylacetylene are added, independently, via solution streams and aged until sufficient formation of cyclopropylethynyl lithium, upon which about one equivalent of compound of formula (II) in a suitable solvent is added and maintained at a temperature below −30° C. for 1–3 hours to form compound (III). Compound (III) may be separated from the reaction as a stable solid by standard methods of work up. An example of standard work up is shown in Example 4.

It is preferred, but not required, that the reagents of this step be added as solution streams; that is they are prepared separately as individual solutions before contact with each other. Reagents which can readily be handled or manipulated as solids can be added to the reaction mixture as such; for example compounds of formula (II) or chiral inducing agents.

Preferred chiral inducing agent for step (2) is 1R,2S-pyrrolidinyl norephedrine.

Preferred alkyl lithium agents for step (2) include n-butyllithium, sec-butyllithium, t-butyllithium, iso-butyllithium, n-hexyllithium and octyllithium. A more preferred alkyl lithium agent is n-hexyllithium.

Preferred solvents and mixtures thereof for step (2) are tetrahydrofuran, hexane, cyclohexane, methylcyclohexane and toluene.

Preferred reaction times in step (2) are about two hours for generation of cyclopropylethynyl lithium and about 1–2 hours for addition of compound (II) to 1R,2S-pyrrolidinyl norephedrine/cyclopropylethynyl lithium.

Preferred temperature ranges for step (2) are about −50 to about −0° C. for generation of cyclopropylethynyl lithium and about −60 to about −40° C. for addition of compound (II) to cyclopropylethynyl lithium/1R,2S-pyrrolidinyl norephedrine solution.

Step 3: Oxidative Cyclization: Preparation of Compound of Formula (IV)

This step comprises reacting a carbinol compound of formula (III) in a suitable solvent with preferably at least about one equivalent of a suitable oxidizing agent at a sufficient temperature for a suitable length of time to form a compound of formula (IV). By way of general guidance, compound (III) in a suitable nonaqueous solvent may be contacted with about one molar equivalent of a suitable oxidizing agent and heated to a temperature for about one to about six hours sufficient to form compound (IV). Compound (IV) may be separated from the reaction as a stable solid by quenching with a suitable nonaqueous solvent, followed by standard methods of work up. An example of standard work up is shown in Example 5. Additionally, Compound (IV) may be carried forward without isolation into Step 4 for the preparation of Compound (V) as shown in Example 6b.

Preferred oxidizing agents for step (3) include p-tetrachlorobenzoquinone and 2,3-dichloro-5,6-dicyano-1,4-benzoquinone.

Preferred solvents and mixtures thereof for step (3) are toluene, heptane, ethyl acetate, methyl-t-butyl-ether, tetrahydrofuran, dichloromethane and cyclohexane. For reactions when 2,3-dichloro-5,6-dicyano-1,4-benzoquinone is used ethanol and methanol are suitable.

Reaction times for step (3) depend on the solvent and temperature. A preferred reaction time for step (3) when the solvent is heptane/ethyl acetate following addition of the oxidizing agent is about four to about six hours.

A preferred temperature range for the addition of oxidizing agent to compound (III) depends on the solvent. A preferred temperature range for step (3) when the solvent is heptane/ethyl acetate is initially about room temperature and, thereafter, reflux temperature.

Step 4: Debenzylation: Preparation of Compound of Formula (V)

This step comprises the reaction of a compound of formula (IV) in a suitable solvent with a suitable strong base at a temperature sufficient to form a compound of formula (V). Since a product of debenzylation of the hemiaminal is an aromatic aldehyde or ketone, depending on the structure of P", the aldehyde or ketone must be trapped or converted by contact with a suitable trapping agent to a material which will not react with compound (V).

Three different methods of trapping an aromatic aldehyde or ketone byproduct are feasible. First, after reacting the hemiaminal (IV) with a strong base to form a compound of formula (V) and an aromatic aldehyde or ketone byproduct, the byproduct can be reduced to the corresponding alcohol with a suitable reducing agent; allowing the amine (V) to be isolated by neutralization of the reaction mixture followed by filtration. Alternatively and second, the byproduct can be trapped by a reagent with greater affinity for the byproduct than the free amine (V), for example, reaction of the byproduct with hydroxyl amine to for a corresponding oxime or, more preferably, reaction of the byproduct with tosyl hydrazide to form the corresponding tosyl hyrazone, wherein the amine (V) can be isolated by careful pH adjustment of the solution as to crystallize or precipitate out the desired amine (V) product. Alternatively and third, the byproduct, when it is an aromatic aldehyde, can be trapped by a reagent which oxidizes the aldehyde to a corresponding acid but will not react with the amine or acetylene moieties of (V); such a trapping agent is hydrogen peroxide under basic conditions.

By way of general guidance, compound (IV) in an aqueous/organic solvent was contacted with a suitable strong base, preferably sodium hydroxide or potassium hydroxide, at sufficient temperature for a suitable length of time to initiate formation of a compound of formula (V) followed by addition of a suitable trapping agent, preferably sodium borohydride, at a temperature sufficient to quantitatively form compound (V) while converting the byproduct aldehyde or ketone to its corresponding alcohol. Compound (V) may be separated from the reaction as a stable solid by quenching the trapping agent, followed by pH adjustment of the solution and standard methods of work up. An example of standard work up is shown in Example 6. Optionally, compound (V) may be carried forward in synthesis of compounds of formula (VI).

Preferred strong bases for step (4) include sodium, potassium, lithium or calcium hydroxides, as well as, metal alkoxides. Most preferably the strong base is sodium hydroxide or potassium hydroxide.

Preferred trapping agents are those which reduce the aromatic aldehyde/ketone byproduct to an alcohol but not react with the amine of compound (V) nor the acetylene of compound (V). Of trapping agents which are reducing agents, a preferred agent is sodium borohydride.

Preferred solvents for step (4) are alcohol mixed with water. Most preferably the solvent is methanol and water.

Preferred reaction time for step (4) is about one to about three hours.

A preferred temperature range for the addition of base to compound (IV) in step (4) is about 0 to about 100° C.; more preferably the temperature range is about 30 to about 60° C., followed by addition of trapping agent.

Step 5: Cyclization: Preparation of Compound of Formula (VI)

This step comprises the cyclization of chiral compound of formula (V) by contacting with a cyclizing agent in a suitable solvent at a temperature sufficient to form a compound of formula (VI). By way of guidance, about one equivalent of compound (V) is contacted with about two equivalents of cyclizing agent and stirred at about 20 to about 25° C. until the reaction was quantitative. Compound (VI) may be separated from the reaction as a stable solid by standard methods of work up. An example of standard work up is shown in Example 7.

Preferred cyclizing agent for step (5) is phosgene.

Preferred solvents in step (5) are heptanes, toluene and tetrahydrofuran. Most preferably the solvent is a mixture of heptanes/tetrahydrofuran.

Preferred temperature range for the addition of cyclizing agent in step (5) is less than or about 0° C.

With a judicious selection of reagents, as is well appreciated to one skilled in the art of organic synthesis, the claimed process can be performed in a straightforward manner to yield the compounds of formulas (II), (III), (IV), (V) and (VI).

The present invention may be further exemplified by reference to Scheme 2 wherein $R^2$=H in an example of a compound of formula (VII).

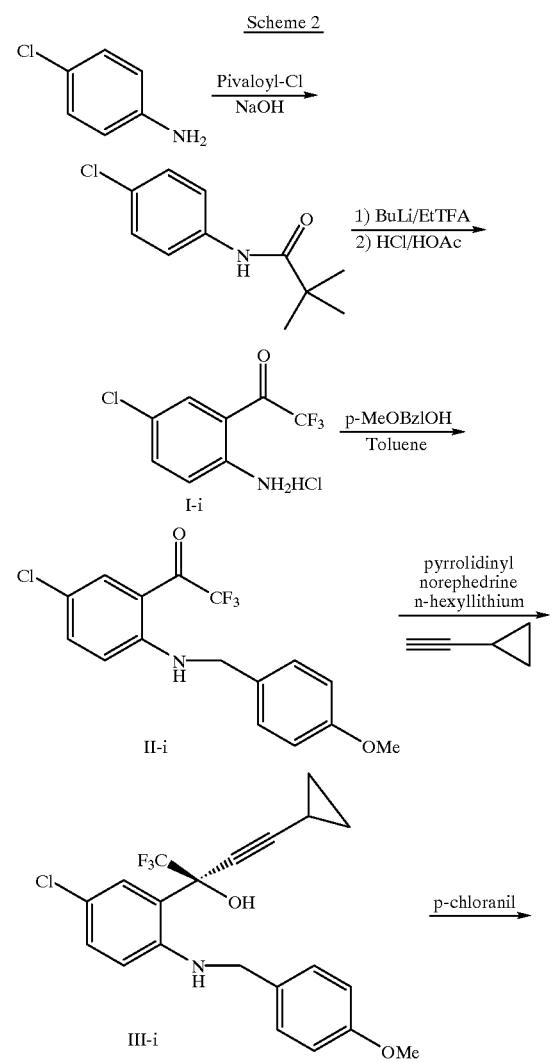

Scheme 2

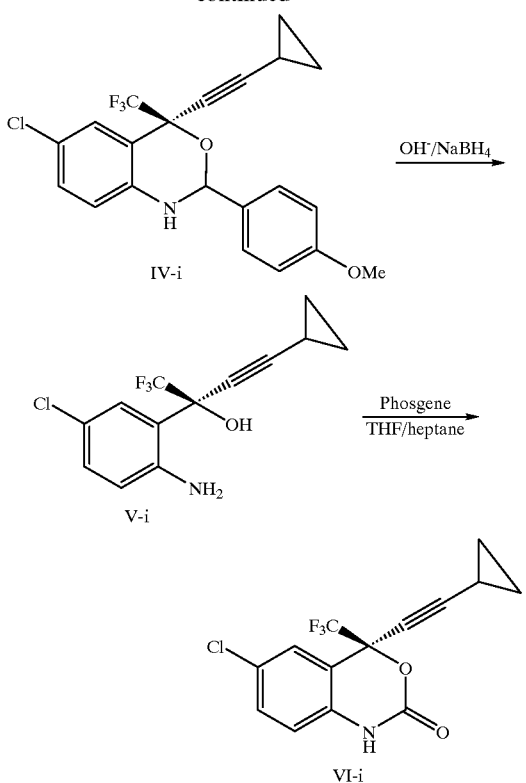

The methods of the present invention, by way of example and without limitation, may be further understood by reference to Scheme 2a. This scheme details further embodiments of the general synthetic method for preparation of a compound of formula (II-i). The methods of Scheme 2a provide for excellent conversion to Compound (II-i) and facile crystallization of the product.

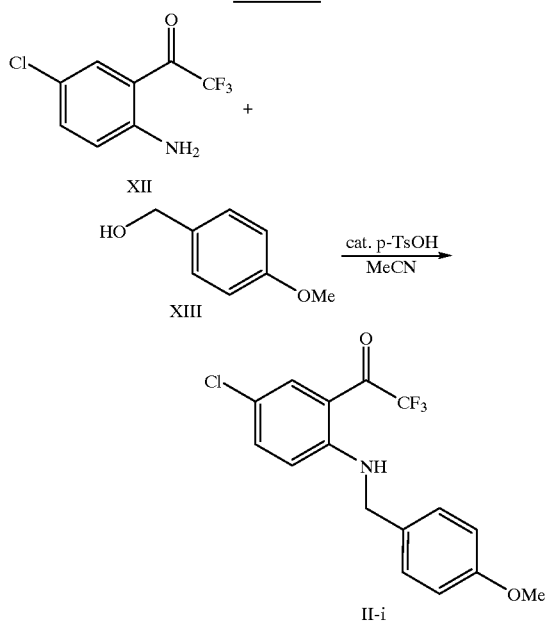

By way of general guidance, a substituted aniline of formula (XII) and p-toluenesulfonic acid are heated and stirred in acetonitrile to a temperature of about 65° C. to about 85° C. to which an acetonitrile solution of a benzyl alcohol of formula (XIII) is added over a period of about 2 hours to about 10 hours, preferably about 3 to about 3 hours; m o re preferably about 3 to about 6 hours. The mole ratio of substituted aniline to p-toluenesulfonic acid is about 1:0.010 to about 1:0.030; more preferably about 1:0.015. The mole ratio of substituted aniline to substituted benzyl alcohol is about 1:1 to about 1:1.2; more preferably about 1:1.1. Upon addition of the benzyl alcohol the reaction mixture is heated and stirred additionally for about 30 minutes to about 4 hours to give a crude solution of the compound of formula (II-i). The crude solution of the compound of formula (II-i) is cooled to a temperature of about 20° C. to about 30° C., preferably about 25° C.; after which seed crystals of (II-i) are added. Upon addition of the seed crystals water is slowly added to form a slurry of the crystalline compound of formula (II-i), while stirring the solution at a temperature of about 30° C. to about 35° C. The slurry is stirred for a reaction time of about 2 hours to about 12 hours at about room temperature after which the slurry is filtered to isolate the crystalline compound of formula (II-i). The crystalline material is washed with a mixture of acetonitrile and water in a volume to volume ratio of about 60:40 to about 40:60; preferably the volume to volume ratio of acetonitrile and water used is about 50:50. Finally, the crystalline material is dried under an inert atmosphere at a temperature of about 50° C.

The methods of the present invention, by way of example and without limitation, may be further understood by reference to Scheme 2b. This scheme details further embodiments of the general synthetic method for preparation of a compound of formula (V-i). The methods of Scheme 2b allow for complete recovery of the 2,3-dichloro-5,6-dicyano-1,4-dihydroxybenzene, allow for less use of NaBH$_4$, and allow for recrystallization to proceed at a much lower temperature. Thus, this method allows for crystallization of a valuable intermediate.

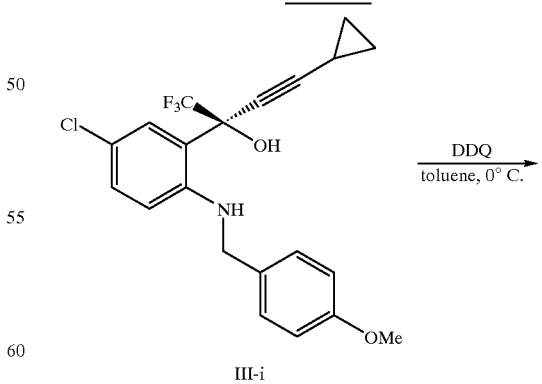

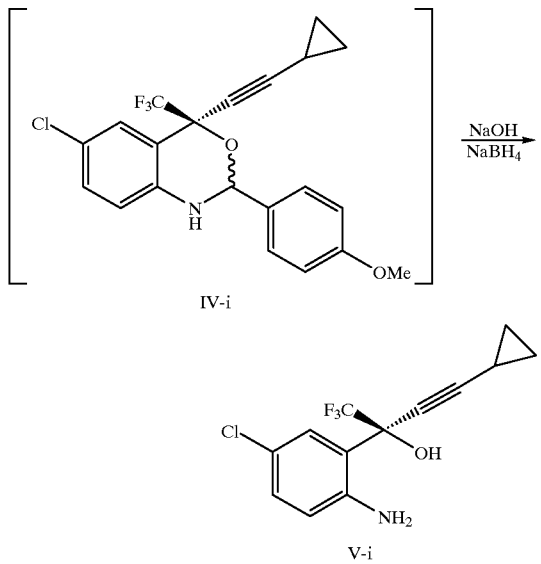

By way of general guidance, a toluene solution of 2,3-dichloro-5,6-dicyano-1,4-benzoquinone is added to a toluene solution of a compound of formula (III-i) while maintaining a reaction temperature of about 0° C. to about 10° C. after which the reaction temperature is maintained at about 0° C. for about 1 hour to form a toluene slurry of 2,3-dichloro-5,6-dicyano-1,4-dihydroxybenzene and a compound of formula (IV-i). The slurry is filtered to remove the 2,3-dichloro-5,6-dicyano-1,4-dihydroxybenzene; the resulting waste cake of the 2,3-dichloro-5,6-dicyano-1,4-dihydroxybenzene is washed with toluene. The filtrate and toluene washings are combined and concentrated in vacuo with addition of methanol to remove most of the toluene and produce the compound of formula (IV-i) in methanol at a temperature of about 40° C. to about 45° C. To this solution an aqueous solution of sodium hydroxide is added dropwise to form a clear solution of the amino alcohol (V-i) and p-methoxybenzaldehyde upon which a solution of NaBH$_4$ in an aqueous solution of sodium hydroxide is added dropwise, all the time maintaining a reaction temperature of about 40° C. to about 45° C. Upon addition of the solution of NaBH$_4$ in an aqueous solution of sodium hydroxide, the reaction solution is stirred for about 30 minutes after which glacial acetic acid is added to neutralize the reaction to a pH of about 8 to about 9. Upon neutralization water is added to form a slurry and the slurry is cooled to about −15° C. to about 0° C. for about 1 hour. The cooled slurry of the amino alcohol (V-i) is filtered and washed with water to give the crude crystalline amino alcohol (V-i) as a pale yellow solid.

It is preferable to recrystallize (V-i) in toluene or a mixture of MTBE-toluene. If recrystallization proceeds in toluene, crude crystalline amino alcohol is dissolved in toluene at a temperature of about 60° C. after which heptane is added to form a slurry of the pure amino alcohol. The amino alcohol slurry is cooled to about 0° C. and maintaining at about 0° C. for about 1 hour after which the pure crystalline amino alcohol is filtered. The pure crystalline amino alcohol is washed with heptane and dried in vacuo.

If recrystallization proceeds in a mixture of MTBE-toluene, crude crystalline amino alcohol is dissolved in a mixture of MTBE-toluene at a temperature of about 20° C. to about 30° C. after which the MTBE is distilled in vacuo from the MTBE-toluene solution. Heptane is added to form a slurry of the pure amino alcohol. The amino alcohol slurry is cooled to about 0° C. and maintaining at about 0° C. for about 1 hour after which the pure crystalline amino alcohol is filtered. The pure crystalline amino alcohol is washed with heptane and dried in vacuo.

The methods of the present invention, by way of example and without limitation, may be further understood by reference to Scheme 3 wherein neither R$^2$ nor R$^3$ is H in an example of a compound of formula (VII). This scheme details further embodiments of the general synthetic method for preparation of compounds of formula (VI) utilizing a very acid labile amino protecting group. Besides gaining high yields of enantiomer excess in the chiral induction step; the subsequent isolation of compound (V) is achieved without chromatography in a one step procedure, rapidly and under very mild room temperature conditions.

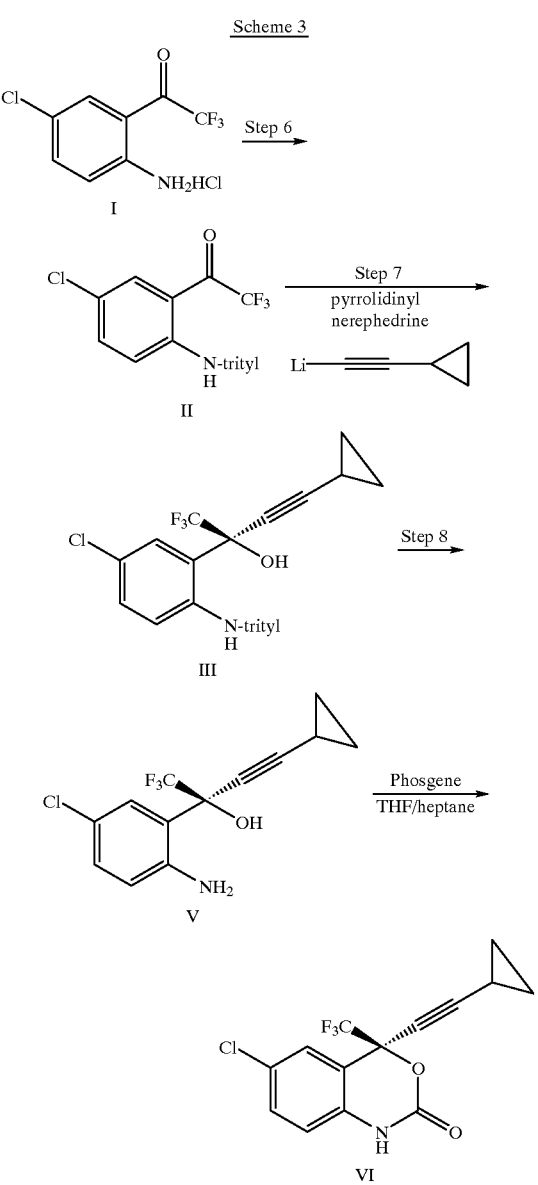

Scheme 3

Step 6: Addition: Preparation of Compound of Formula (II) wherein R$^2$ and R$^3$ of compound (VII) or (VIII) are not H.

This step is conducted by reacting a compound of formula (I), after converting to the free base, in a suitable solvent at a suitable temperature with a compound (VII) or (VIII), wherein neither $R^2$ nor $R^3$ is H, in the presence of a suitable acid catalyst to form a compound of formula (II). By way of general guidance, compound (I) in an aqueous/organic solvent at about room temperature may be neutralized with base to about pH 7, contacted with about 1 molar equivalent of a compound (VII) or (VIII), wherein neither $R^2$ nor $R^3$ is H, preferably trityl alcohol, additionally contacted with about 0.1 to about 5.0 mole % of a suitable acid catalyst and heated to a temperature sufficient to form compound (II). Compound (II) may be separated from the reaction as a stable solid by standard methods of work up. An example of standard work up is shown in Example 11. Optionally, compound (II) may be carried forward in synthesis of compounds of formula (III).

Compound (VII) or (VIII), wherein neither $R^2$ nor $R^3$ is H is preferably trityl alcohol or methoxy substituted trityl alcolhol.

Preferred acid catalysts for step (6) include HCl, methane sulfonic acid, sulfuric acid, trifluroacetic acid and p-toluene-sulfonic acid. More preferred acid catalysts are methane sulfonic acid and p-toluene-sulfonic acid.

Preferred solvents and mixtures thereof for step (6) are toluene, dioxane, cyclohexane, acetonitrile, ethyl acetate, dimethoxyethane, 2-propanol and acetic acid.

A preferred temperature range for step (1) is about room temperature to about 120° C. More preferably when compound (VIII) is trityl alcohol the temperature range is about 60 to about 90° C.

It is understood that one skilled in the art can determine the preferred reaction time of Step 1 as dependent on temperature, acid catalyst and P group. Generally, the reaction time is 0.5 to 12 hours.

Step 7: The chiral induction step in Scheme 3 is similar to the chiral induction step of Sceme 1; an example of the synthesis of a compound of formula (III) wherein P is a trityl group is shown in Example 12.

Step 8: Detritylation: Preparation of Compound of Formula (V)

This step comprises the reaction of a compound of formula (III), wherein the amino protecting group is very acid labile, eg. trityl, in a suitable solvent with about 0.1 to about 2.0 equivalents of a suitable acid at a sufficiently mild temperature to form a compound of formula (V). The byproduct of detritylation is an aromatic alcohol and subsequently need not be trapped as in step (4) of Scheme 1, above. Compound (V) may be separated from the reaction as a stable solid by pH adjustment of the solution and standard methods of work up. An example of standard work up is shown in Example 13. Optionally, compound (V) may be carried forward in synthesis of compounds of formula (VI).

Acceptable amino protecting groups for step (8) are trityl, p-methoxytrityl, 4,4'-dimethoxytrityl as well as non-trityl groups, such as, 2,4-dimethoxy benzyl and 4,4'-dimethoxybenzhydryl. A preferred amino protecting group is trityl.

Preferred strong acids for step (8) include HCl, HBr methane sulfonic acid, trifluroacetic acid and p-toluene-sulfonic acid. A more preferred acid is HCl or trifluoroacetic acid.

Preferred solvents for step (8) are lower alkyl alcohols and need not be anhydrous, such as methanol, ethanol and propanols. Most preferably the solvent is methanol.

A preferred temperature range for the addition of acid to compound (III) in step (8) is about 0 to about 50° C.; more preferably the temperature range is about 0 to about 30° C.

The preparation of cyclopropylacetylene, (X), which is a reactant in the formation of a compound of formula (III), is demonstrated in Scheme 4.

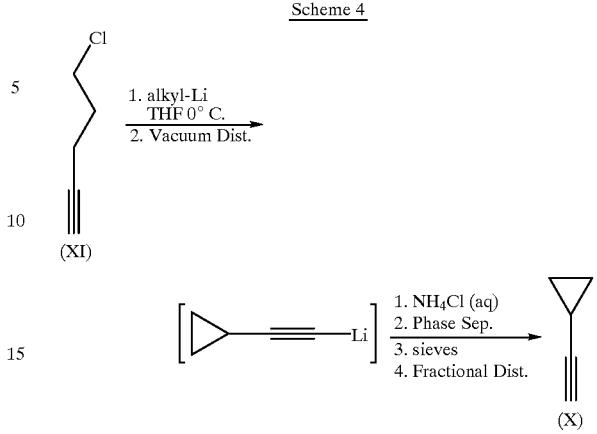

Scheme 4

The preparation of cyclopropylacetylene, (X), by Scheme 4 is further illustrated in Example 15. This preparation of cyclopropylacetylene provides for about 100% conversion of chloropentyne (XI) and greater than about 90% yield of cyclopropylacetylene, thus enabling the product (X) to be used in a solution stream in the preparation of a compound of formula (III).

The following examples are meant to be illustrative of the present invention. These examples are presented to exemplify the invention and are not to be construed as limiting the invention's scope.

EXAMPLE 1

Preparation of N-(4-chlorophenyl)-2,2-dimethyl propanamide

4-Chloroaniline (52.7 kg, 413 mol) was dissolved in a mixture of t-butyl methyl ether (180 kg), 30% aqueous sodium hydroxide (61.6 kg, 463 mol) and water (24.2 kg), then cooled to 15° C. To the resulting slurry was charged trimethylacetyl chloride (52.2 kg, 448 mol) over 1 h, keeping the temperature below 40° C. After stirring 30 min at 30° C. the slurry was cooled to −10° C. and held for 2 hours. The product was collected by filtration, washed with a solution of 90/10 water/methanol (175 kg), then dried in vacuo to give 85 kg (97% yield) of the title compound as a crystalline solid: mp 152–153° C.; $^1$H NMR (300 MHz, CDCl$_3$) δ 7.48 (d, J=9 Hz, 2H) 7.28 (d, J=9 Hz, 2H); $^{13}$C NMR (75 MHz, CDCl$_3$) d 176.7, 136.6, 129.1, 128.9, 121.4, 39.6, 27.6.

Preparation of N-(4-fluorophenyl)-2,2-dimethyl propanamide

It is understood by one skilled in the art of organic synthesis that 4-fluoroaniline can be readily substituted for 4-chloroaniline above to synthesize this compound.

EXAMPLE 2

Preparation of 4-Chloro-2-trifluoroacetylaniline, hydrochloride hydrate

N-(4-Chlorophenyl)-2,2-dimethyl propanamide (36.7 kg, 173 mol) was charged to a solution of TMEDA (20.2 kg, 174 mol) in anhydrous t-butyl methyl ether (271.5 kg) and cooled to −20° C. To the cold slurry was added 2.7 N n-butyllithium in hexane (101.9 kg, 393 mol) while keeping the temperature below 5° C. After aging 2 hr at 0 to 5° C., the solution was cooled below −15° C. then rapidly reacted with ethyl trifluoroacetate (34.5 kg, 243 mol). After 30 min, the resulting solution was quenched into 3N HCl (196 L, 589 mol) keeping the temperature below 25° C. After removal of the aqueous phase, the organic solution was concentrated by distilling approximately 200 L of solvent. Acetic acid (352 kg) was added while distilling 325 kg solvent under 100 mm vacuum. After cooling the solution to 30° C., 12 N HCl (43.4 kg, 434 mol) was added and the mixture heated to 65 to 70° C. and held 4 hours. The resulting slurry was cooled to 5° C and the product was collected by filtration, washed with ethyl acetate (50.5 kg) and dried in vacuo to give 42.1 kg (87%) of the title compound as a white crystalline solid: mp 159–162 dec; $^1$H NMR (300 MHz, DMSO-d$_6$) d 7.65–7.5 (complex, 2H), 7.1 (d, J=8 Hz, 1H), 7.0 (brs, 3H); $^{19}$F NMR (282 MHz, DMSO-d$_6$) δ −69.5.

It is understood by one skilled in the art of organic synthesis that CF$_3$CF$_2$CO$_2$Et or CF$_3$CF$_2$CF$_2$CO$_2$Et can be readily substituted for ethyl trifluoracetate above to synthesize additional homologues.

EXAMPLE 3-a
Preparation of 4-Chloro-2-trifluoroacetylaniline

4-Chloro-2-trifluoroacetylaniline, hydrochloride hydrate (17.1 g, 62 mmol) was stirred in a mixture of toluene (100 mL) and water (50 mL). The mixture was neutralized to pH 7 with saturated NaHCO$_3$. The organic phase was concentrated in vacuo and the residue recrystallized from heptane to give 12.5 g (91%) of the title compound as yellow needles: mp 98–99° C.; $^1$H NMR (300 MHz, CDCl$_3$) δ 7.70 (t, J=2 Hz, 1H), 7.32 (dd, J=2, 9 Hz, 1H), 6.7 (d, J=9 Hz, 1H), 6.44 (brs, 2H); $^{13}$C NMR (75 MHz CDCl$_3$) δ 180.0, 151.6, 136.9, 130.1 , 120.9, 119.0, 116.8, 111.4; $^{19}$F NMR (282 MHz, CDCl$_3$) δ−70.3.

EXAMPLE 3
Preparation of N-((4'-Methoxy)benzyl)-4-chloro-2-trifluoroacetylaniline. Compound (II-i)

To a slurry of 4-Chloro-2-trifluoroacetylaniline, hydrochloride hydrate (40.0 kg, 144 mol) in toluene (140 kg) and water (50 L) was added 30% NaOH (18 kg) to pH 7.0. After removing the aqueous phase, 4-methoxybenzyl alcohol (20 kg, 144 mol) and TsOH (1.0 kg, 5.3 mol) were added. The solution was heated to reflux and the water/toluene azeotrope (30 L) distilled. The solution was cooled to room temperature and washed with saturated brine (80 kg). The organic solution was concentrated in vacuo to a volume of 35–40 L, then diluted with THF (52 kg). The weight percent of the title compound in toluene/THF was calculated by HPLC to be 43%. The yield based on HPLC weight% analysis was 47.7 kg (96%). An analytical sample was obtained by removing the solvent in vacuo and recrystallizing from heptane: mp 82–84° C.; $^1$H NMR (300 MHz, CDCl$_3$) δ 9.04 (s,1H), 7.74 (d, J=2 Hz, 1H), 7.35 (dd, J=2, 9 Hz), 7.24 (d, J=8 Hz, 2H), 6.91 (d, J=8 Hz, 2H), 6.75 (d, J=9 Hz, 1H), 4.43 (d, J=6 Hz, 2H), 3.79 (s, 3H); $^{13}$C NMR (75 MHz, CDCl$_3$) δ 180.5, 159.2, 151.9, 137.4, 130.8, 128.9, 128.4, 119.9, 117.0, 114.5, 114.4, 111.3, 55.3, 46.6.

EXAMPLE 4
Preparation of (S)-5-Chloro-α-(cyclopropyl-ethynyl)-2-[(4-methoxyphenyl)methyl]-amino]α-(trifluoromethyl) benzenemethanol. Compound (III-i)

To a toluene solution of (1R,2S)-pyrrolidinyl norephedrine (80 kg, containing 60.7 mol (1R,2S)-pyrrolidinyl norephedrine) was charged triphenylmethane (100 g). The solution was concentrated in vacuo to about half the original volume. Anhydrous THF (35 kg) was added and the solution chilled with the cooling jacket set at −50° C. When the temperature reached −20° C., n-hexyllithium (33 wt % in hexanes, 33.4 kg, 119.5 mol) was charged while maintaining the temperature below 0° C. To the resulting red solution was charged a solution of cyclopropylacetylene (30 wt % in THF/hexanes/toluene; containing about 4 kg, 65 mol of cyclopropylacetylene) while maintaining an internal temperature below −20° C. The resultant solution was aged at −45 to −50° C. for 1 hour. To the cold solution was charged a solution of N-((4'-Methoxy)benzyl)-4-chloro-2-trifluoroacetylaniline (43 wt % in THF/toluene; containing about 10 kg, 28.8 mol of N-((4'-Methoxy)benzyl)-4-chloro-2-trifluoroacetylaniline) while maintaining a reaction temperature below −40° C. After aging the mixture at −43±3° C. for 1 h, the reaction was quenched into 140 kg 1N HCl, pre-chilled to 0° C. The organic layer was separated and extracted twice with 25 kg portions of 1N HCl, twice with 40 kg water, then concentrated in vacuo to a volume of about 29 L. Toluene (47 kg) was added and the solution concentrated to a volume of 28 to 30 L. Heptane (23 kg) was charged and the mixture cooled and held at −5° C. for 4 hours. The product was filtered, washed twice with 10 kg portions of heptane and dried in vacuo to give 10 kg (85%) of the title compound as an off-white solid: mp 163–165° C.; [a]$^{25}$D +8.15° (c 1.006, MeOH); $^1$H NMR (300 MHz, CDCl$_3$) δ 7.55 (brs, 1H), 7.23 (d, J=8 Hz, 2H), 7.13 (dd, J=3, 9 Hz, 1H), 6.86 (d, J=8 Hz, 2H), 6.59 (d, J=8 Hz, 1H), 4.95 (bs, 1H), 4.23 (s, 2H), 3.79 (s, 3H), 2.39 (m, 1H), 1.34 (m, 1H), 0.84 (m, 2H), 0.76 (m, 2H); $^{13}$C NMR (75 MHz, CDCl$_3$) δ 158.9, 145.5, 130.6, 130.3, 130.2, 128.6, 125.9, 122.0, 121.6, 119.5, 114.8, 114.1, 94.0, 75.2, 74.7, 70.6, 55.3, 48.0, 8.6, 8.5, −0.6; $^{19}$F NMR (282 MHz, CDCl$_3$) δ −80.19.

EXAMPLE 5
Preparation of (S)-6-Chloro-4-(cyclopropylethynyl)-1,4-dihydro-4-(trifluoromethyl)-2-(4'-methoxyphenyl)-3,1-benzoxazine. Compound (IV-i)

To a solution of heptane (295.5 kg) and ethyl acetate (32.5 kg) was added p-chloranil (57 kg, 232 mol) and (S)-5-Chloro-α-(cyclopropylethynyl)-2-[(4-methoxyphenyl)methyl]-amino]-α-(trifluoromethyl)benzenemethanol (89 kg, 217 mol). The mixture was refluxed with good agitation for 5.5 h then diluted with ethyl acetate (64.1 kg) and cooled to 30° C. Tetracholorophydroquinone was removed by filtration and washed with a mixture of heptane (104.7 kg) and ethyl acetate (31 kg). The filtrate was partially concentrated by distillation of 260 L solvent, then diluted with heptane (177 kg) and cooled to −10 to −15° C. The resulting slurry was filtered and the product washed with heptane (41 kg) and dried on the filter to less than 20 wt % heptane (by loss on drying). The yield of (IV), calculated by HPLC, was 71 kg (80%). An analytical sample was obtained by trituration of the sample with 1N NaOH, followed by recrystallization from hexane/ethyl acetate: mp 130–131.7° C.; $^1$H NMR (300 MHz, DMSO-d$_6$) δ 7.46 (d, J=9 Hz, 2H), 7.28–7.21 (m, 3H), 7.0 (d, J=9 Hz, 2H), 6.85 (d,J=9 Hz, 1H), 5.52 (s, 1H), 3.78 (s, 3H), 1.52–1.47 (m, 1H), 0.90–0.84 (m, 2H), 0.72–0.68 (m, 1H); $^{13}$C NMR (75 MHz, DMSO-d$_6$) δ 160.3, 143.8, 129.6, 129.3, 128.9, 125.8, 123.1, 121.7, 118.1, 117.8, 113.8, 93.6, 80.9, 74.1, 70.3, 55.2, 8.5, 8.4, −1.07; $^{19}$F NMR (282 MHz, CDCl$_3$) δ 157.5.

EXAMPLE 6
Preparation of Compound (V-i): (S)-5-Chloro-α-(cyclopropylethynyl)-2-amino-α-(trifluoromethyl) benzenemethanol Crude (S)-5-Chloro-4-(cyclopropylethynyl)-1,4-dihydro-4-(trifluoromethyl)-2-(4'methoxyphenyl)-3,1-benzoxazine (71 kg calculated dry weight) was charged to a mixture of methanol (301 kg), 30% NaOH (121 kg) and water (61 L). The mixture was heated to 60° C. to give a clear solution then cooled to 30° C. A solution of sodium borohydride (3.2 kg, 84.2 mol) in 0.2 N NaOH (29 L) was added to the methanolic solution over 20 min, keeping the temperature below 35° C. After 30 min, excess borohydride was quenched with acetone (5.8 kg) and the solution diluted with water (175 L) then neutralized to pH 8 to 9 with acetic acid. The resulting slurry was cooled to about 0° C., filtered and the product washed with water then dried in vacuo at 40° C. The crude product was reslurried with a mixture of toluene (133 kg) and heptanes (106 kg) initially at 25° C., then with cooling below −10° C. The product was filtered, washed with heptanes (41 kg) and dried in vacuo at 40° C. to give 44.5 kg (88%) as an off-white/pale yellow crystalline solid. An analytical sample was recrystallized from t-butyl methyl ether/heptane: mp 141–143° C.; $[a]^{25}D$ −28.3° (c 0.106, MeOH); 1H NMR (300 MHz, CDCl$_3$) δ 7.54 (d, J=2 Hz, 1H), 7.13 (dd, J=9, 2 Hz, 1H), 6.61 (d, J=9 Hz, 1H), 4.61 (brs, 1H), 4.40 (brs, 1H), 1.44–135 (m, 1H), 0.94–0.78 (m, 2H): $^{13}$C NMR (75 MHz, DMSO-d$_6$) δ 146.7, 129.4, 129.0, 124.3, 118.4, 118.07, 118.05, 92.3, 72.6, 71.0, 8.2, 8.1, −1.1; $^{19}$F NMR (282 MHz CDCl$_3$) δ −80.5.

EXAMPLE 6b

Preparation of Compound (V-i) from Compound (III-i) Without Isolation of Compound (IV-i) in Preceeding Step of Synthesis (S)-5-Chloro-α-(cyclopropylethynyl)-2-amino-α-(trifluoromethyl)benzenemethanol To a slurry of DDQ (9.42 g, 41.5 mmol) in t-butyl methyl ether (33 ml) at 10° C. was added a solution of (S)-5-chloro-α-(cyclopropylethynyl)-2-(4-methoxyphenyl)methyl]amino]-α-(trifluoromethyl)benzenemethanol (16.38 g, 40 mmol). After 5 minutes the resulting slurry was filtered at 30° C. and the resulting solids washed with 5 ml t-butyl methyl ether. The filtrate was washed with 5% aqueous sodium bicarbonate then partially concentrated by distilling 70 ml solvent. Methanol (25 ml) was added followed by distilling 25 ml of solvent. Methanol (25 ml) and 6N NaOH (4 ml) were added followed by distillation of 20 ml of solvent. 4N NaOH (26 ml) was added and the mixture heated briefly to 58° C. then cooled to 30° C. A solution of sodium borohydride (0.60 g, 15.9 mmol) in 0.5 N NaOH (6 mL) was added. After 15 minutes, water (45 ml) was added followed by acetone (1 ml). After 0.5 hours, acetic acid (12 ml, 210 mmol) was added to a pH of 7.5. The resulting slurry was cooled to about 0° C., filtered and the product was washed with water then dried in vacuo at 40° C. The crude product was reslurried at room temperature with methylcyclohexane, cooled to about 0° C. and filtered. This material was further purified by recrystallization from t-butyl methyl ether/hexanes to give 9.95 g (86%) as a white solid. The physical characteristics were identical with product prepared by the two step (p-chloranil/NaBH$_4$) process. (Example 6, above)

EXAMPLE 7

Preparation of (S)-6-Chloro-4-(cyclopropyl-ethynyl)-1,4-dihydro-4-(trifluoromethyl)-2H-3,1-benzoxazine-2-one. Compound (VI-i)

(S)-5-Chloro-α-(cyclopropylethynyl)-2-amino-α-(trifluoromethyl)benzenemethanol (15.7 kg, 54.3 mol) was dissolved in a mixture of heptanes (32 kg) and THF (52 kg) below −10° C. Phosgene (~8.0 kg, 80 mol) was directly fed below the surface over about 1 h, keeping the temperature below 0° C. The resulting slurry was warmed to 20–25° C. and held 1 hour. Methanol (6.5 kg, 203 mol) was added and the solution stirred about 30 min. Heptanes (97 kg) was added and ~140 L of solvent was distilled under reduced pressure. Heptanes (97 kg) and THF (22 kg) were added and the solution washed with 5% aqueous sodium bicarbonate (15 L), followed by water (15 L). The solution was warmed to 50° C. and filtered into a clean reactor, followed by a 40 kg heptanes rinse. The solution was concentrated under reduced pressure, diluted with heptanes (22 kg) and cooled below −10° C. The product was filtered, washed with heptanes (37 kg) and dried in vacuo at 90–100° C. to give 16.0 kg (95%) as an off-white to slightly pinkish solid. HPLC: 99.8 area %: mp 139–141° C.; $[a]^{25}D$ −94.10 (c 0.300, MeOH); 1H NMR (400 MHz, DMSO-d$_6$) δ 11.05 (s, 1H), 7.54 (dd, J=2.5, 7 Hz, 1H), 7.43 (d, J=2.5 Hz, 1H), 6.99 (d, J=7 Hz, 1H), 1.58 (m, 1H), 0.92 (m, 2H), 0.77 (m, 2H); $^{13}$C NMR (100 MHz, DMSO-d$_6$) δ 146.23, 134.71, 132.04, 126.93, 126.57, 122.24, 116.83, 114.08, 95.63, 77.62, 65.85, 8.48, 8.44, −1.32; $^{19}$F NMR (282 MHz, DMSO-d$_6$) δ −81.1.

EXAMPLE 8

Preparation of N-((3',4'-Dimethoxy)benzyl)-4-chloro-2-trifluoroacetylaniline

4-Chloro-2-trifluoroacetylaniline (4.96 g, 40 mmol) and 3,4-dimethoxybenzyl alcohol (7.39 g, 44 mmol) were added to 2-propanol (40 mL). TsOH (76 mg, 0.4 mmol) was added and the mixture heated to 60° C. and held 3.5 hours. The solution was concentrated in vacuo to ½ the original volume, diluted with water (10 mL) and stirred at room temperature. The resulting slurry was filtered and the product dried in vacuo at 30° C. to give 10.16 g (68%) of the title compound as a yellow powder. An analytical sample was obtained by recrystallization from acetonitrile: mp 82–84° C.; $^1$H NMR (CDCl$_3$) δ 9.05 (brs, 1H), 7.75 (brt, J=2 Hz, 1H), 7.35 (dd, J=2, 8 Hz, 1H), 6.8 (d, J=8 Hz, 3H), 6.75 (d, J=8 Hz, 1H), 4.43 (d, J=5 Hz, 2H), 3.88 (s, 3H), 3.87 (s, 3H); $^{13}$C NMR (CDCl$_3$) δ 179.9, 151.9, 149.4, 148.7, 137.4, 130.8, 130.8, 130.7, 129.4, 119.4, 114.5, 111.5, 111.4, 110.3, 56.1, 56.0, 47.0; $^{19}$F NMR (CDCl$_3$) δ 69.61.

EXAMPLE 9

Preparation of (S)-5-Chloro-α-(cyclopropylethynyl)-2-[(3,4-dimethoxyphenyl)methyl]-amino]-α-(trifluoromethyl) benzenemethanol A 17.2 wt % solution of (1R,2S)-pyrrolidinyl norephedrine (254 g, 213 mmol) was concentrated by distilling 160 mL of solvent at atmospheric pressure. Triphenylmethane (0.2 g, 0.8 mmol) was added and the solution was cooled to room temperature. THF (130 mL) was added and the solution was cooled to −20° C. n-Hexyllithium (2.0 M solution in hexane, 203 mL, 0.406 mol) was added while maintaining the temperature below 0° C. The mixture turned red after the addition of 108 mL. A 16 weight % solution of cyclopropylacetylene (103 g, 0.25 mol) was added until the solution decolorized. The solution was stirred at −5 to 0° C. for 20 min and then cooled to −45° C., at which point compound N-((3',4'-Dimethoxy)benzyl-4-chloro-2-trifluoroacetylaniline (29.7 g, 81.8 mmol) predissolved in 50 mL THF was added. After 1 h at 45° C., the mixture was quenched into 2 N HCl (400 mL). The organic layer was washed twice with 2N HCl (100 mL) then concentrated in vacuo. Toluene (150 mL) was added and the mixture was concentrated to a volume of 80 mL. Heptane (100 mL) was added and the solvent ratio (determined by GC analysis) heptane:toluene was adjusted to 60:40 by adding 43 mL of toluene. After crystallization, the product was filtered and recrystallized from toluene: heptane (3:1) to give 23.1 g (64%) of the title compound as a pale yellow solid: mp 128–129.5° C.; $[a]^{25}D+11.00°$ (c 0.300, MeOH); $^1$H NMR (300 MHz, CDCl$_3$) δ 7.56 (m, 1H), 7.13 (dd, J=9, 3 Hz, 1H), 6.84 (m, 3H), 6.58 (d, J=9 Hz, 1H), 4.24 (m, 2H), 3.85 (s, 3H), 3.83 (s, 3H), 1.34 (m, 1H), 0.90–0.74 (m, 4H; $^{13}$C NMR (75 MHz, DMSO-d$_6$) δ 148.8, 147.8, 146.3, 131.4, 129.8, 129.4, 124.3, 119.1, 118.9, 118.2, 113.4, 111.8, 110.9, 92.7, 73.8, 70.9, 55.5, 55.3, 46.5, 8.2, 8.1, −1.1; $^{19}$F NMR (282 MHz CDCl$_3$) δ −80.0.

EXAMPLE 10

Preparation of (S)-6-Chloro-4-(cyclopropylethynyl)-1,4-dihydro-4-(trifluoromethyl)-2-(3',4'-dimethoxyphenyl)-3,1-benzoxazine To a solution of (S)-5-Chloro-α-(cyclopropylethynyl)-2-[(3,4-dimethoxyphenyl)methyl]-amino]-α-(trifluoromethyl) benzenemethanol (2.68 g, 6.1 mmol) in methanol (10 mL) at 40° C. was added DDQ (1.40 g, 6.1 mmol). The resulting slurry was cooled 30 min in an ice bath and filtered. The product was washed with 5 mL cold methanol and dried in vacuo to give 2.36 g (88%) of title compound: mp 172–175° C.; $^1$H NMR (300 MHz, CDCl$_3$) δ 7.48 (s, 1H), 7.18 (dd, J=2, 9 Hz, 1H) 7.13 (d, J=7 Hz, 1H), 7.10 (s, 1H), 6.87 (d, J=7 Hz, 1H), 6.70 (d, J=9 Hz, 1H), 5.62 (d, J=4 Hz, 1H), 4.33 (d, J=4 Hz, 1H), 3.90 (s, 3H), 3.87 (s, 3H), 1.33 (m, 1H), 0.90–0.72 (complex, 4H); $^{13}$C NMR (75 MHz, CDCl$_3$) δ 150.1, 149.3, 141.5, 129.9, 129.7, 127.3, 125.4, 125.0, 121.2, 120.8, 119.7, 119.0, 111.0, 109.7, 93.5, 81.4, 70.3, 56.0, 8.7, −0.4; $^{19}$F NMR (282 MHz, CDCl$_3$) δ −79.2.

EXAMPLE 11

Preparation of N-Triphenylmethyl-4-chloro-2-trifluoroacetylaniline. Method A

4-Chloro-2-trifluoroacetylaniline (22.4 g, 100 mmol), trityl chloride (30.0 g, 107 mmol), triethylamine (11.6 g, 115 mmol) and DMAP (0.5 g, 4 mmol) were dissolved in DMF (50 mL) and held 14 h at 60° C. The resulting slurry was cooled to room temperature, diluted with 20 mL water and filtered to give 35.9 g (77%) of title compound. An analytical sample was obtained by recrystallization from acetonitrile: mp 165–167° C.; $^1$H NMR (CDCl$_3$) δ 10.4 (brs, 1H), 7.71 (brt, J=2 Hz, 1H), 7.3 (brs, 15 H), 6.9 (dd, J=2, 8 Hz, 1H), 6.27 (d, J=8 Hz, 1H) $^{13}$C NMR (75 MHz, CDCl$_3$) δ 180.5, 151.2, 144.1, 135.7, 130.7, 130.6, 129.2, 128.9, 128.7, 128.6, 128.5, 128.2, 128.0, 127.7, 127.5, 122.9, 120.3, 119.3, 119.1, 115.2, 112.3, 111.3, 71.9; $^{19}$F NMR (282 MHz, CDCL$_3$) δ −69.5.

Preparation of N-Triphenylmethyl-4-chloro-2-trifluoroacetylaniline. Method B

4-Chloro-2-trifluoroacetylaniline, hydrochloride hydrate (84.4 g, 304 mmol), cyclohexane (350 mL), MTBE (95 mL), and water (100 mL) were stirred at room temperature. The resulting slurry was neutralized with 30 mL 10 N NaOH. To the organic phase was added trityl alcohol (91.0 g, 350 mmol) and TsOH (0.36 g, 1.9 mmol). The mixture was heated to reflux and 300 mL of solvent was distilled. Acetonitrile. (350 mL) and diisopropylethyl amine (0.5 mL) were added and the distillation continued to remove 220 mL additional solvent. The solution was cooled in an ice bath and the product filtered to give 126.5 g (89%) of product with the same spectral and physical properties as the sample prepared in Method A.

EXAMPLE 12

Preparation of 5-Chloro-α-(cyclopropylethynyl)-2-triphenylmethyl]-amino]-α-(trifluoromethyl) benzenemethanol To a solution of cyclopropylacetylene (3.15 g, 48 mmol) and (1R,2S)-pyrrolidinyl norephedrine (10.9 g, 53 mmol) in THF (50 mL) was added 2N n-hexyllithium (46 mL, 92 mmol) keeping the temperature below 0° C. N-Triphenylmethyl-4-chloro-2-trifluoroacetylaniline (9.32 g, 20 mmol), dissolved in THF (20 mL) was added to the anionic solution and held at −45 to −50° C. for 1 h, then quenched with 1 N citric acid (92 mL). The organic layer was separated, dried with sodium sulfate and concentrated to an oil. Crystallization from heptane/toluene gave 6.34 g (60%) of the title compound: mp 180–182° C.; [α]$^{25}$D +7.77° (c 1.004, CH$_3$CN); $^1$H NMR (300 MHz, CDCl$_3$) δ 7.53 (d, J=2 Hz, 1H), 7.4–7.1 (complex, 16 H), 6.67 (dd, J=2,7 Hz 1H), 6.05 (d, J=7 Hz, 1H), 3.17 (brs, 1H), 1.07 (m, 1H), 0.72 (m, 2H), 0.62 (m, 2H); $^{13}$C NMR (75 MHz, CDCl$_3$) δ 143.7, 129.1, 129.0, 128.8, 128.1, 126.9, 126.0, 122.2, 120.7, 118.7, 118.3, 94.7, 74.0, 71.6, 70.2, 8.4, 8.3, −0.8; 19F NMR (282 MHz, CDCl$_3$) δ −79.9.

EXAMPLE 13

Preparation of (S)-5-Chloro-α-(cyclopropyl-ethynyl)-2-amino-α-(trifluoromethyl)benzenemethanol. A One Step Debenzylation 5-Chloro-α-(cyclopropylethynyl)-2-(triphenylmethyl)-amino-α-(trifluoromethyl)benzenemethanol (5.32 g, 10 mmoL) was dissolved in methanol (25 mL) and reacted with 12 N HCl (0.5 mL) at room temperature. After 15 min, 2N NaOH (2 mL) and water (20 mL) were added. The aqueous methanolic solution was extracted with cyclohexane (22 mL) followed by hexanes (20 mL) then partially concentrated in vacuo and neutralized with acetic acid to pH 7. The product was filtered, washed with water and dried to give 2.65 g (92%): mp 140–143° C. The spectroscopic properties are identical with material made by Example 6.

EXAMPLE 14

Synthesis of (1R,2S)-Pyrrolidinyl norephedrine

To a mixture of n-butanol (227 kg), water (144 kg) and potassium carbonate (144 kg, 1043 mol), was added (1R, 2S)-norephedrine (68.6 kg, 454 mol). The mixture was heated to 90° C. and 1,4-dibromobutane (113.4 kg, 525 mol) was added over 2 hours. The reaction was refluxed 5 h then cooled to 40° C. Water (181 kg) was added and the phases separated at 30° C. To the organic phase was added 12 N HCl (54.3 kg, 543 mol). The solution was heated to reflux and 150 L of distillate removed at 200 to 300 mm. Toluene (39.5 kg) was added at 70° C. and the resulting slurry cooled to 0–5° C. for crystallization. The product was collected, washed twice with toluene (39 kg each) and dried under a nitrogen purge to give 83.6 kg of the title compound as its hydrochloride salt. The hydrochloride salt was charged to toluene (392 kg) and water (42 kg) and treated with 30% NaOH (approximately 55 kg, 414 mol) to a pH greater than 12. After removal of the lower aqueous phase, the organic solution was partially concentrated by distilling 140 L of solvent to give a 20 wt % solution of the title compound in toluene. The calculated yield was 50 kg (75%). An analytical sample was obtained by concentrating the toluene solution of the title compound in vacuo then recrystallizing from heptane: mp 46–48° C.

EXAMPLE 15

Preparation of Cyclopropylacetylene (X)

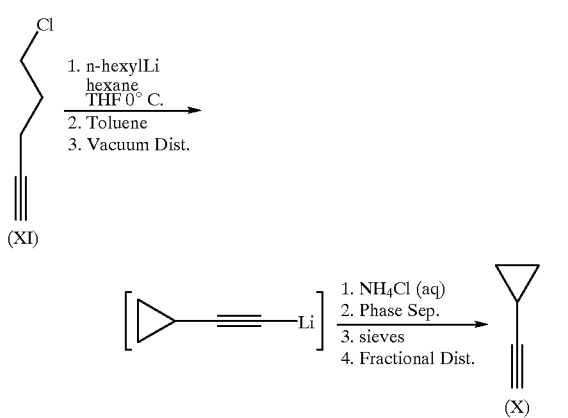

A mixture of 5-chloro-1-pentyne, (XI), (23.0 kg, 224 mol) and anhydrous THF (150 kg) is cooled to −20° C. n-Hexyllithium (2.3 eq.; 158 kg of 30 wt. %) in hexane is added into the mixture at such a rate as to not allow the temperature to go over 5° C. (approximately 2 hours). During the second half of the n-hexyllithium addition the temperature must remain above −5° C. to prevent an accumulation of the organolithium and a dangerously exothermic induction reaction. The reaction is aged at −5 to 0° C. for 2 hours, until GC analysis indicates at least 99% conversion. Toluene (35 to 40 kg) is then added and the reaction is concentrated under vacuum until the volume is reduced to ~⅓ of original volume. The mixture is heated (to −40° C.) over the course of the concentration to maintain a good rate of distillation. The mixture is then cooled to 15 to −20° C. and a solution of ammonium chloride (11 to 12 kg) in 50 to 60 L water is added at such a rate as to not allow the temperature to go above 10° C. After separation of the aqueous layer (approximately 70 kg), the reaction mixture is circulated through a tower containing 15 kg of 3 Å molecular sieves until the water content is ~300 ppm or lower as determined by Karl Fisher analysis. The dried organic solution is then distilled through a column packed with steel wool at atmospheric pressure, collecting cyclopropylacetylene, (X), as a solution in THF/toluene/hexane. The calculated yield is 14.0 kg.

EXAMPLE 16

Synthesis of p-Methoxybenzyl-ketoaniline, II-i

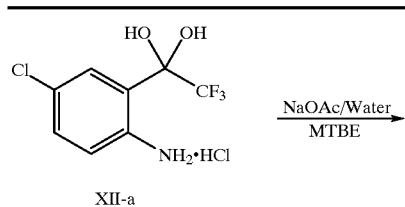

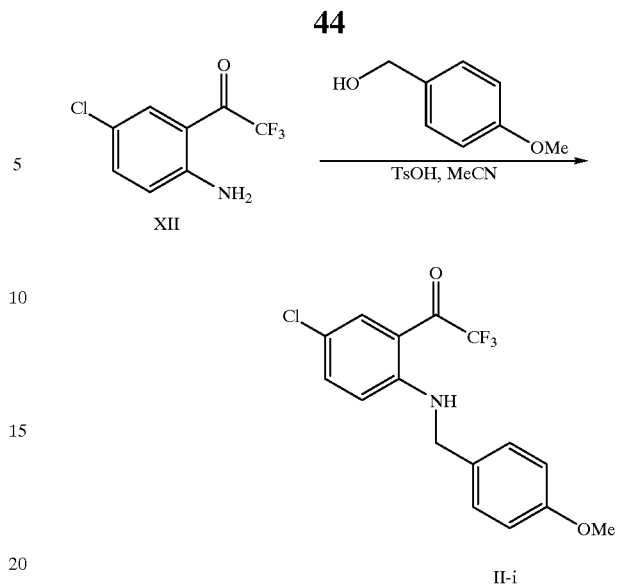

| Materials | mw | amount | mol. | equiv. |
|---|---|---|---|---|
| Ketoaniline-HCl(94%) XII-a | 278.05 | 3,000 g | 10.14 | |
| t-Butyl methyl ether (MTBE) | | 18 L | | |
| Sodium acetate | 82.03 | 1,419 g | 17.3 | 1.7 |
| D.I. water | | 7.2 + 11 + 10 L | | |
| Ketoaniline, XII | 223.57 | 2,245 g | 10.04 | 1.00 |
| 4-Methoxybenzyl alcohol | 138.17 | 1,526 g | 11.04 | 1.10 |
| p-Toluenesulfonic acid-H₂O | 190.22 | 28.65 g | 0.15 | 0.015 |
| Acetonitrile | | 28 + 3 + 10 L | | |

| Product | Theory | | | |
|---|---|---|---|---|
| II-i | 343.73 | 3,451 g | 10.04 | 1.00 |

Step A: Preparation of the ketoaniline, XII

In a 50 L extractor was charged D.I. water (3.6 L) and sodium acetate (1,419 g). The mixture was stirred at room temperature for 5–10 min. until all sodium acetate was dissolved. t-Butyl methyl ether (18 L) was then added and followed by the addition of substrate XII-a (3,000 g). The heterogeneous mixture was stirred at room temperature for 20–30 min. or until solid disappeared. The pH of the aqueous layer should be in the range of 4.0–6.0, otherwise HCl (6 N) or NaOH (5 N) was used to adjust the pH to the desired range. The batch was settled and two layers were separated. The organic layer was washed with D.I. water (3.6 L) and transferred to a 50 L three-necked round bottom reaction flask which equipped with mechanical stirrer and a thermocouple. The solution was concentrated to about 6–7 L, flushed with acetonitrile (2×12 L) and the final batch volume was adjusted with acetonitrile to 8–8.5 L. Ketoaniline XII in acetonitrile (the solution KF<300 mM) was assyed by HPLC: a total 2,245 g (10.04 mol) of XII was obtained after neutralization with a recovery of 99%.

Step B: Preparation of II-i

Under nitrogen, p-toluenesulfonic acid monohydrate (28.65 g, 0.15 mol) was added to a solution of ketoaniline XII in acetonitrile (8–8.5 L, 10.04 mol) in the 50 L flask. The reaction mixture was heated to 70° C. with stirring. 4-Methoxybenzyl alcohol (1,526 g, 11.04 mol) in acetonitrile (3 L) was added over 5 h, keeping the batch temperature at 68–72° C. The reaction was monitored by HPLC and it was normally complete within 2 h after the addition of the alcohol.

The batch was cooled to room temperature and seeded. Bright yellow crystalline solid gradually formed. The slurry was then aged at room temperature for 1–2 h with stirring. Water (11 L) was added slowly over 2 h at 35° C. After aging at room temperature for another 1–2 h, the solid was filtered, washed with 50/50 acetonitrile/water (2×10 L). The wet cake was dried under vacuum (50° C., 28 in., 24 h) to give the product II-i (3,354 g, 99 wt %, 95% yield based on LC assay and 99.5+LC area %). The KF of the dry cake was less than 0.5 mole %.

EXAMPLE 17
Synthesis of p-Methoxybenzyl-ketoaniline, II-i

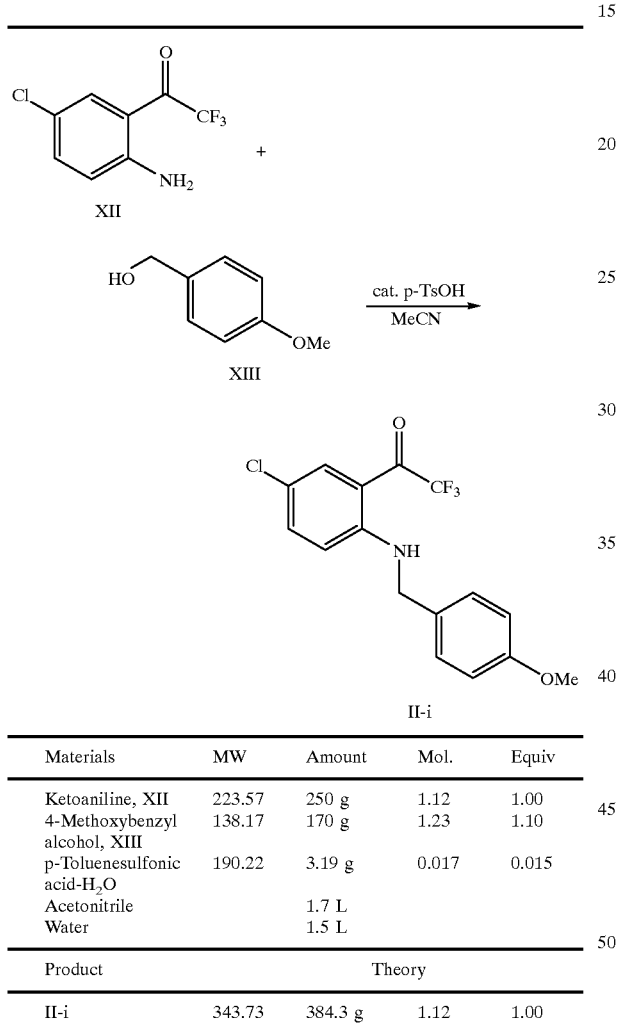

| Materials | MW | Amount | Mol. | Equiv |
|---|---|---|---|---|
| Ketoaniline, XII | 223.57 | 250 g | 1.12 | 1.00 |
| 4-Methoxybenzyl alcohol, XIII | 138.17 | 170 g | 1.23 | 1.10 |
| p-Toluenesulfonic acid-H$_2$O | 190.22 | 3.19 g | 0.017 | 0.015 |
| Acetonitrile | | 1.7 L | | |
| Water | | 1.5 L | | |

| Product | | Theory | | |
|---|---|---|---|---|
| II-i | 343.73 | 384.3 g | 1.12 | 1.00 |

Under nitrogen, to a 3 L three-necked round bottom flask equipped with a mechanical stirrer, an addition funnel and a thermocouple was charged with acetonitrile (900 mL), ketoaniline XII (250 g, 1.12 mol) and p-toluenesulfonic acid monohydrate (3.19 g, 0.017 mol). The reaction mixture was then heated to reflux with stirring. 4-Methoxybenzyl alcohol (170 g, 1.23 mol) in acetonitrile (400 mL) was added via an addition funnel over a period of 4 h. The batch was kept under reflux at 85° C. The reaction was monitored by HPLC and it normally was complete within 1 hour after the addition of 4-methoxybenzyl alcohol.

The batch was cooled to 45–50° C. and seeded. Water (1.1 L) was added in 30–40 min with stirring and the batch turned cloudy. Bright yellow crystalline solid gradually formed during the process. The batch was aged at room temperature for another 1–2 h with stirring. The solid was isolated with filtration and the wet cake was washed with 50/50 acetonitrile/water (800 mL). It gave the product II-i (361 g, 96.3 wt %, 90% yield and >99.5 A %) after drying. The water content in the cake was 0.6 mole %.

EXAMPLE 18
Synthesis of Amino Alcohol, V-i

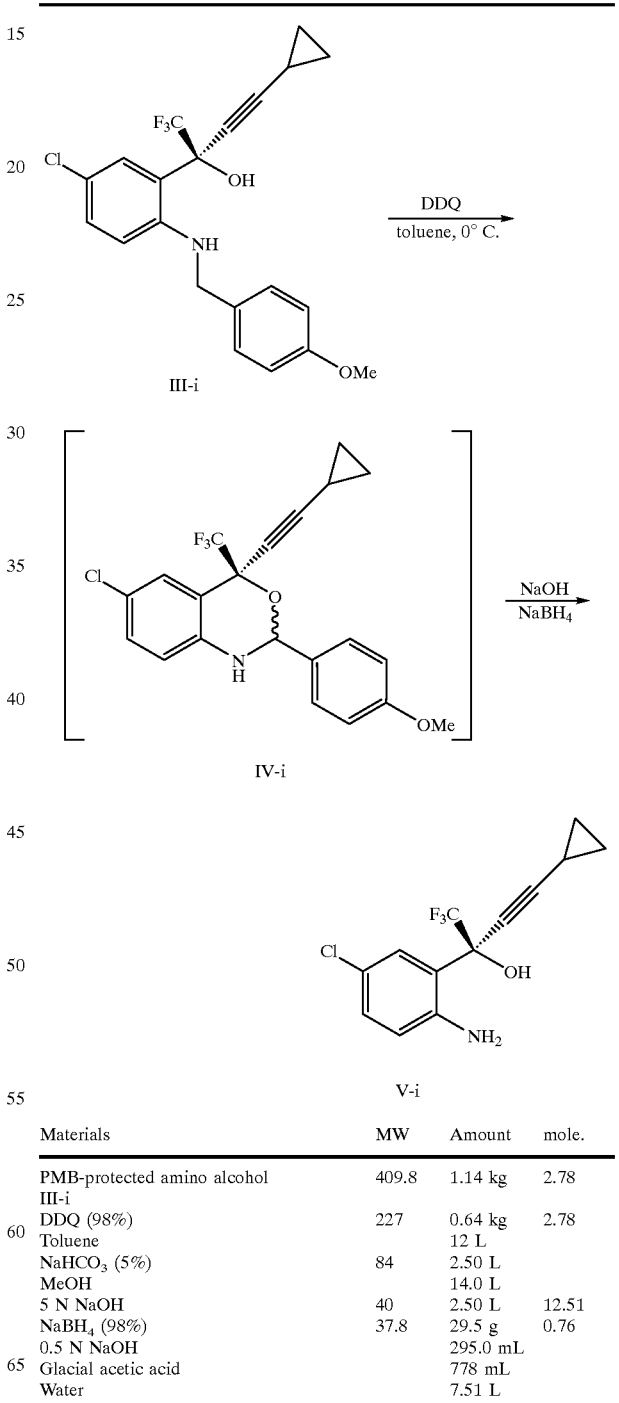

| Materials | MW | Amount | mole. |
|---|---|---|---|
| PMB-protected amino alcohol III-i | 409.8 | 1.14 kg | 2.78 |
| DDQ (98%) | 227 | 0.64 kg | 2.78 |
| Toluene | | 12 L | |
| NaHCO$_3$ (5%) | 84 | 2.50 L | |
| MeOH | | 14.0 L | |
| 5 N NaOH | 40 | 2.50 L | 12.51 |
| NaBH$_4$ (98%) | 37.8 | 29.5 g | 0.76 |
| 0.5 N NaOH | | 295.0 mL | |
| Glacial acetic acid | | 778 mL | |
| Water | | 7.51 L | |

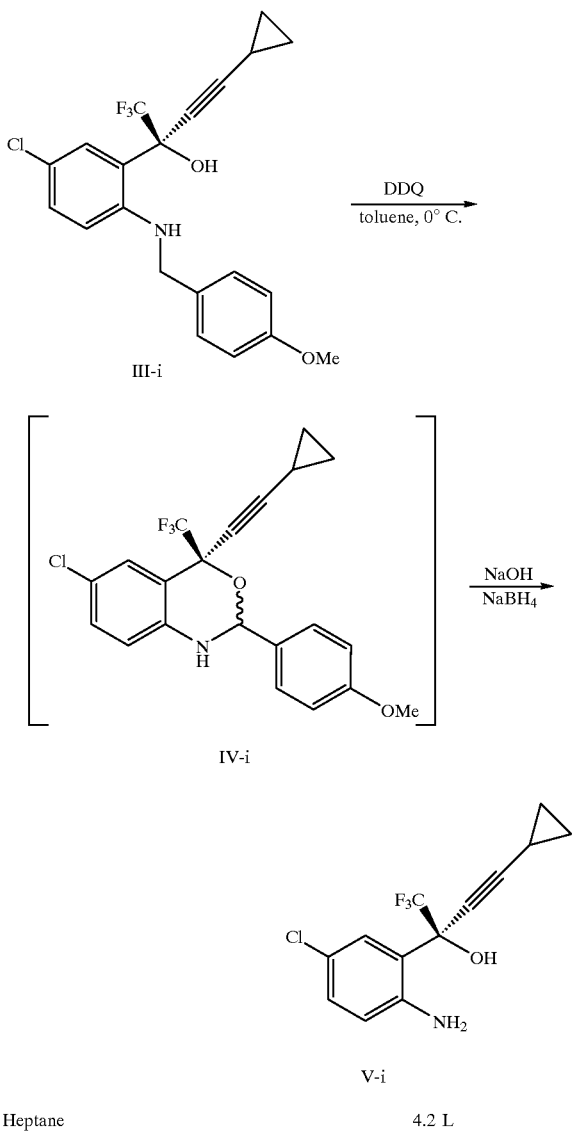

Step A: Preparation of the amino alcohol, V-i 2,3-Dichloro-5,6-dicyano-1,4-benzoquinone (DDQ) was dissolved in toluene (3.42 L) at ~30° C. and was charged under N₂ dropwise to a slurry of the PMB protected amino alcohol in toluene (5.7 L) at 0° C., maintaining the temperature between 0–10° C. The resulting mixture was aged at ambient temperature for 2 h and filtered. The waste solid was washed with toluene (3×0.8 L). The filtrate and wash were combined, washed with aqueous 5% NaHCO₃ and concentrated in vacuo to ~2 L at ~40° C. MeOH (9 L) was added portionwise and the solution was concentrated to ~2 L. The total volume of the solution was adjusted to 5 L with methanol. The solution was heated at 40° C. and 5 N NaOH (2.5 L) was added over ~10 min. The resulting clear solution was maintained at 40° C. for 30 min. A solution of NaBH₄ in 0.5 N NaOH was added dropwise, maintaining the temperature at 40–45° C. The mixture was stirred at ambient temperature for 15 min, cooled to ~19° C., and neutralized with glacial acetic acid to pH ~8.4 with an external cooling bath to maintain the temperature at 20–25° C. Water was added over 15 min. The mixture was maintained at 23° C. for 1 h and filtered. The solid was washed with one cake volume of water and dried in vacuo to give a pale yellow solid: 832 g.

Step B: Recrystallization of the amino alcohol, V-i

The crude product was charged into toluene (2.78 L) and heated quickly to 60–64° C. to give a clear solution. The solution was allowed to cool to room temperature while heptane (4.17 L) was added slowly (in 1 h). The resulting slurry was cooled to 0° C. and held for 1 h. The solid was collected by filtration, washed with heptane (1 solid volume), and dried in vacuo to give 734.2 g of the desired product as a white solid.

Alternate Step B: Recrystallization of, V-i

The crude product was charge into toluene (1.6 L) at 20–25° C. MTBE (0.66 L) was added to give a clear solution. The solution was concentrated in vacuo to ~1.6 L. Toluene (0.5 L) was added. The solution was concentrated to ~1.6 L again to give a slurry. Heptane (2.4 L) was charged into the slurry over 1 h. The resulting mixture was cooled to 0° C., aged for 1 h, and filtered. The solid was washed with one solid volume of heptane and dried in vacuo to give the desired product as a white solid.

Although the present invention has been described with respect to specific embodiments, the details of these embodiments are not to be construed as limitations. Various equivalents, changes and modification may be made without departing from the spirit and the scope of this invention, and it is understood that such equivalent embodiments are part of this invention. The present invention may be embodied in other specific forms without departing from the spirit or essential attributes thereof and, accordingly, reference should be made to the appended claims as further indicating the scope of the invention.

What is claimed is:

1. A process for the preparation of an amino alcohol compound of formula (V-i):

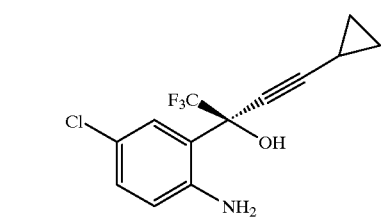

comprising (1) adding a toluene solution of 2,3-dichloro-5,6-dicyano-1,4-benzoquinone to a toluene solution of a compound of formula (III-i):

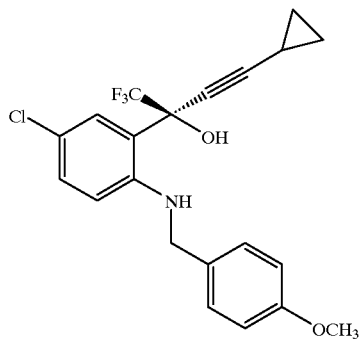

(III-i)

while maintaining a reaction temperature of about 0° C. to about 10° C.;

(2) maintaining the reaction temperature at about 0° C. for about 1 hour to form a toluene slurry of 2,3-dichloro-5,6-dicyano-1,4-dihydroxybenzene and a compound of formula (IV-i):

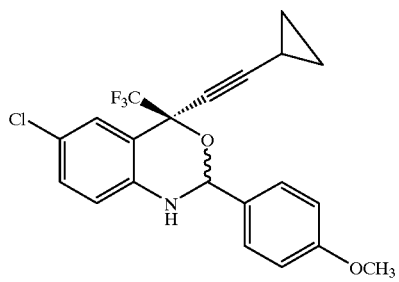

(IV-i)

(3) filtering the slurry to remove the 2,3-dichloro-5,6-dicyano-1,4-dihydroxybenzene;
(4) washing the 2,3-dichloro-5,6-dicyano-1,4-dihydroxybenzene waste cake with toluene;
(5) combining the filtrate and toluene washings;
(6) concentrating in vacuo the filtrate and toluene solution of the compound of formula (IV-i) with methanol to remove most of the toluene;
(7) adding dropwise to the compound of formula (IV-i) in methanol at a temperature of about 40° C. to about 45° C. an aqueous solution of sodium hydroxide forming a clear solution of the amino alcohol and p-methoxybenzaldehyde;
(8) adding dropwise to the clear solution of the amino alcohol a solution of $NaBH_4$ in an aqueous solution of sodium hydroxide maintaining a reaction temperature of about 40° C. to about 45° C.;
(9) stirring the reaction mixture for about 30 minutes;
(10) neutralizing the reaction with glacial acetic acid to a pH of about 8 to about 9;
(11) adding water to form a slurry;
(12) cooling the slurry to about −15° C. to about 0° C. for about 1 hour; and
(13) filtering the cooled slurry of the amino alcohol and washing with water to give the crude crystalline amino alcohol as a pale yellow solid.

2. The process for the preparation of pure crystalline amino alcohol compound of formula (V-i) as recited in claim 1 comprising the additional steps of:

(1) dissolving the crude amino alcohol in toluene at a temperature of about 60° C.;
(2) adding heptane to the toluene solution of the crude amino alcohol to form a slurry of the pure amino alcohol;
(3) cooling the amino alcohol slurry to about 0° C. and maintaining at 0° C. for about 1 hour;
(4) filtering the pure crystalline amino alcohol;
(5) washing the pure crystalline amino alcohol with heptane; and
(6) drying the pure crystalline amino alcohol in vacuo.

3. The process for the preparation of pure crystalline amino alcohol compound of formula (V-i) as recited in claim 1 comprising the additional steps of:

(1) dissolving the crude amino alcohol in a mixture of MTBE-toluene at a temperature of about 20° C. to about 30° C.;
(2) distilling in vacuo the MTBE from the MTBE-toluene solution of the crude amino alcohol;
(3) adding heptane to the toluene solution of the crude amino alcohol to form a slurry of the pure amino alcohol;
(4) cooling the amino alcohol slurry to about 0° C. and maintaining at 0° C. for about 1 hour;
(5) filtering the pure crystalline amino alcohol;
(6) washing the pure crystalline amino alcohol with heptane; and
(7) drying the pure crystalline amino alcohol in vacuo.

* * * * *